(12) United States Patent
Saito

(10) Patent No.: US 10,891,737 B2
(45) Date of Patent: Jan. 12, 2021

(54) MEDICAL IMAGE PROCESSING DEVICE, ENDOSCOPE SYSTEM, DIAGNOSIS SUPPORT DEVICE, AND MEDICAL SERVICE SUPPORT DEVICE

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/716,279

(22) Filed: Dec. 16, 2019

(65) Prior Publication Data

US 2020/0118274 A1 Apr. 16, 2020

Related U.S. Application Data

(63) Continuation of application No. PCT/JP2018/022866, filed on Jun. 15, 2018.

(30) Foreign Application Priority Data

Jul. 14, 2017 (JP) .................................. 2017-137731

(51) Int. Cl.
*G06T 7/11* (2017.01)
*G06T 7/00* (2017.01)

(52) U.S. Cl.
CPC .............. *G06T 7/11* (2017.01); *G06T 7/0012* (2013.01); *G06T 2207/10024* (2013.01); *G06T 2207/10068* (2013.01); *G06T 2207/10152* (2013.01)

(58) Field of Classification Search
CPC ..................... G06T 7/11; G06T 7/0012; G06T 2207/10024; G06T 2207/10068;
(Continued)

(56) References Cited

U.S. PATENT DOCUMENTS

2010/0010831 A1* 1/2010 Fueyo ................. G06F 19/3481
705/3
2010/0106002 A1* 4/2010 Sugiyama ................. G06T 9/20
600/410
(Continued)

FOREIGN PATENT DOCUMENTS

EP 2517614 A1 10/2012
JP 2007325641 A 12/2007
(Continued)

OTHER PUBLICATIONS

International Search Report issued in PCT/JP2018/022866; dated Jul. 31, 2018.
(Continued)

*Primary Examiner* — Michael Lee
(74) *Attorney, Agent, or Firm* — Studebaker & Brackett PC

(57) ABSTRACT

There are provided a medical image processing device, an endoscope system, a diagnosis support device, and a medical service support device that can provide appropriate diagnosis support information from a region of interest by appropriately extracting the region of interest. An image acquisition unit acquires a medical image obtained from the image pickup of an object to be observed. A region-of-interest extraction section extracts a first region of interest as a region of interest from the medical image. A region-of-interest change section performs correction processing for correcting the first region of interest to a second region of interest. A user interface receives an instruction given to the region-of-interest change section. The correction processing includes the enlargement, the reduction, or the position change of the first region of interest.

30 Claims, 12 Drawing Sheets

(58) Field of Classification Search
CPC .......... G06T 2207/10152; A61B 5/055; A61B 1/0005; A61B 1/00039; A61B 1/00009; A61B 6/03; A61B 8/00; H04N 2005/2255
USPC .......................................................... 348/65
See application file for complete search history.

(56) References Cited

U.S. PATENT DOCUMENTS

| | | | |
|---|---|---|---|
| 2012/0274754 A1 | 11/2012 | Tsuruoka | |
| 2013/0314520 A1* | 11/2013 | Ishihara | A61B 1/045 348/68 |
| 2014/0028821 A1 | 1/2014 | Tanaka et al. | |
| 2014/0334698 A1 | 11/2014 | Tanaka et al. | |
| 2015/0036903 A1* | 2/2015 | Jerebko | G06T 11/008 382/131 |
| 2016/0012605 A1* | 1/2016 | Itai | G06K 9/52 382/131 |
| 2017/0084031 A1* | 3/2017 | Iwasaki | A61B 6/469 |
| 2018/0144475 A1* | 5/2018 | Hoi | A61B 6/5205 |
| 2018/0289246 A1 | 10/2018 | Tabata et al. | |

FOREIGN PATENT DOCUMENTS

| | | |
|---|---|---|
| JP | 2011067486 A | 4/2011 |
| JP | 2011-255006 A | 12/2011 |
| JP | 2012157384 A | 8/2012 |
| JP | 2013180024 A | 9/2013 |
| JP | 2014-132958 A | 7/2014 |
| WO | 2013140667 A1 | 9/2013 |
| WO | 2014073527 A1 | 5/2014 |
| WO | 2017/104046 A1 | 6/2017 |

OTHER PUBLICATIONS

International Preliminary Report on Patentability issued in PCT/JP2018/022866; completed Sep. 20, 2019.

The extended European search report issued by the European Patent Office dated Jun. 5, 2020, which corresponds to European Patent Application No. 18831878.6-1122 and is related to U.S. Appl. No. 16/716,279.

An Office Action; "Notice of Reasons for Refusal," mailed by the Japanese Patent Office dated Oct. 13, 2020, which corresponds to Japanese Patent Application No. 2019-529006 and is related to U.S. Appl. No. 16/716,279; with English language translation.

* cited by examiner

MEDICAL IMAGE PROCESSING DEVICE, ENDOSCOPE SYSTEM, DIAGNOSIS SUPPORT DEVICE, AND MEDICAL SERVICE SUPPORT DEVICE

CROSS-REFERENCE TO RELATED APPLICATIONS

This application is a Continuation of PCT International Application No. PCT/JP2018/022866 filed on Jun. 15, 2018, which claims priority under 35 U.S.C § 119(a) to Japanese Patent Application No. 2017-137731 filed on Jul. 14, 2017. Each of the above application(s) is hereby expressly incorporated by reference, in its entirety, into the present application.

BACKGROUND OF THE INVENTION

1. Field of the Invention

The present invention relates to a medical image processing device, an endoscope system, a diagnosis support device, and a medical service support device that extract a region of interest from a medical image.

2. Description of the Related Art

A medical image processing device, which uses a medical image as with a processor device for an endoscope to be built into an endoscope system, is being spread in the current medical field. Further, a method, which includes extracting a region of interest where there is a possibility of a lesion part from a medical image and acquiring diagnosis support information about a disease state by performing image analysis for the extracted region of interest, has been performed in recent years. The acquired diagnosis support information is displayed on a display unit, such as a monitor, to be provided to a user.

For example, in WO2013/140667A, a plurality of regions of interest are extracted from a medical image and the plurality of extracted regions of interest are classified into several attributes. The classified attributes are provided to a user as diagnosis support information. Further, in JP2012-157384A, a plurality of regions of interest are extracted from a medical image and the degree of risk based on the grade corresponding to the state of a lesion part is set for each region of interest. Different colors are displayed for the respective degrees of risk, so that the set degrees of risk are provided to a user as diagnosis support information.

SUMMARY OF THE INVENTION

As described above, the diagnosis support information finally provided to a user greatly depends on the extraction results of the regions of interest extracted from the medical image. Particularly, since there is also an endoscope that acquires the image of an object to be observed while being moved in the lumen, there is a case where an object to be observed is not fixed and a region of interest cannot be accurately fixed to a target position. Further, in a case where matters and the like adhering to the surface of a mucous membrane adhering to an object to be observed appear in the medical image, there is a case where a region of interest cannot be accurately extracted. In a case where a region of interest cannot be appropriately extracted as described above, defective diagnosis support information is consequentially provided to a user.

An object of the invention is to provide a medical image processing device, an endoscope system, a diagnosis support device, and a medical service support device that can provide appropriate diagnosis support information from a region of interest by appropriately extracting the region of interest.

A medical image processing device according to an aspect of the invention comprises an image acquisition unit that acquires a medical image obtained from image pickup of an object to be observed, a region-of-interest extraction section that extracts a first region of interest as a region of interest from the medical image, a region-of-interest change section that performs correction processing for correcting the first region of interest to a second region of interest, and a user interface that receives an instruction given to the region-of-interest change section by a user.

It is preferable that the correction processing includes at least one of enlargement, reduction, or position change of the first region of interest. It is preferable that the region-of-interest change section performs addition processing for adding a third region of interest to a position different from a position of the first region of interest or deletion processing for deleting the first region of interest. It is preferable that the user interface receives an instruction to perform the correction processing, the addition processing, or the deletion processing.

It is preferable that the region-of-interest extraction section calculates a first feature quantity from the medical image and extracts a region where the first feature quantity is in a first region extraction range as the region of interest, and the region-of-interest extraction condition is a condition about the first region extraction range. It is preferable that the region-of-interest extraction section calculates a first feature quantity and a second feature quantity from the medical image and extracts the region of interest on the basis of a region where the first feature quantity is in a first region extraction range and a region where the second feature quantity is in a second region extraction range, and the region-of-interest extraction condition is conditions about the first region extraction range and the second region extraction range. It is preferable that the user interface receives an instruction to change the region-of-interest extraction condition.

It is preferable that the medical image processing device further comprises a feature quantity-selection section performing feature quantity-selection processing for selecting a feature quantity, which is to be used for the extraction of the region of interest, from a plurality of feature quantities, and the region-of-interest extraction section calculates the feature quantity selected from the medical image by the feature quantity-selection section and extracts the region of interest on the basis of the calculated feature quantity. It is preferable that the user interface receives an instruction for the feature quantity-selection processing.

It is preferable that a first medical image and a second medical image different from each other are included in the medical image, the region-of-interest change section performs the correction processing on a region of interest extracted from the first medical image, and the region-of-interest extraction section extracts a region of interest from the second medical image by using region correction information about the correction processing. It is preferable that the medical image processing device further comprises a region correction information-storage section storing the region correction information. It is preferable that the medical image processing device further comprises a diagnosis support information-calculation section calculating diagnosis support information from the first region of interest or the second region of interest.

According to the invention, it is possible to provide appropriate diagnosis support information from a region of interest by appropriately extracting the region of interest.

DESCRIPTION OF THE PREFERRED EMBODIMENTS

First Embodiment

Figure 1:
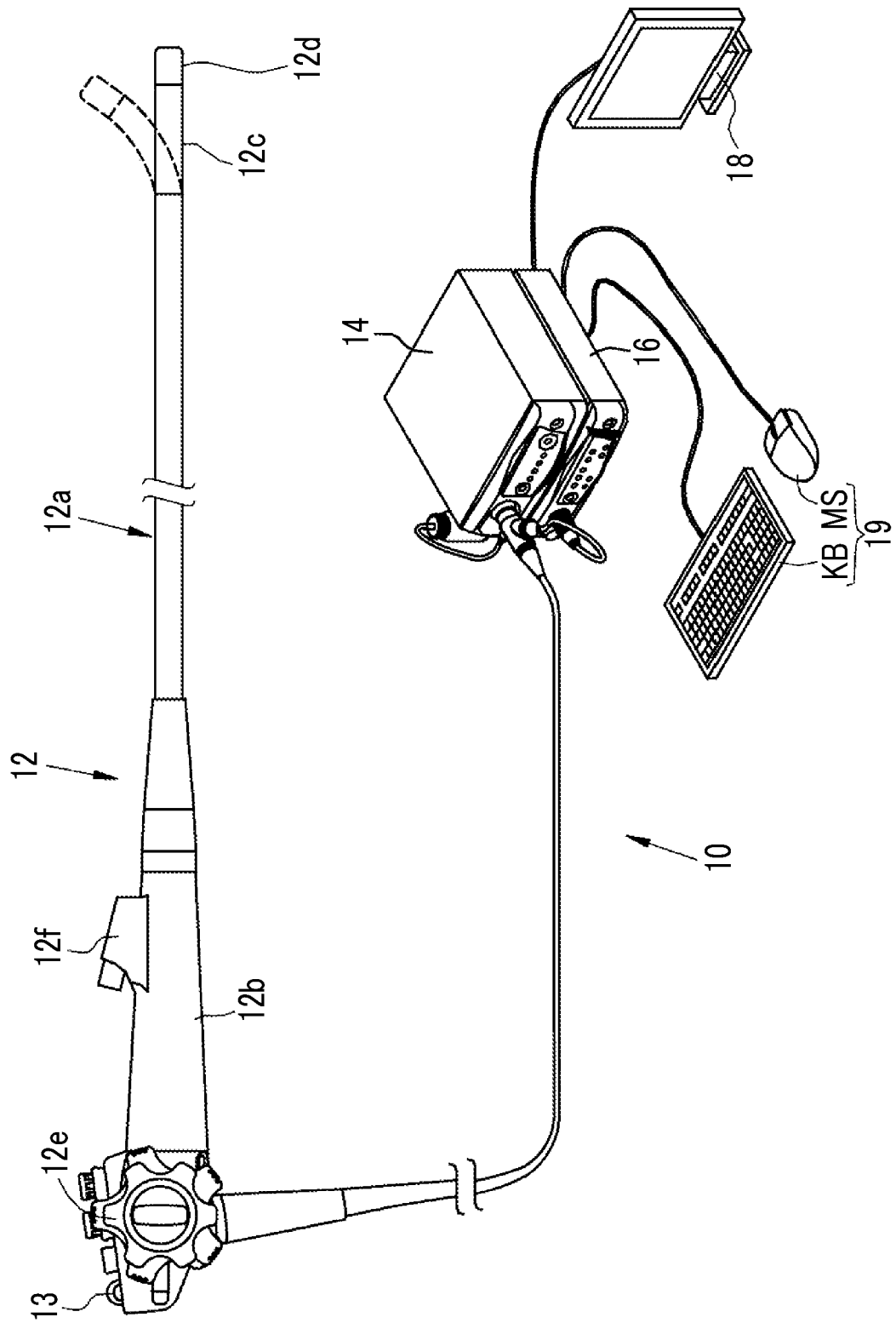
FIG. 1 is a diagram showing the appearance of an endoscope system.

As shown in FIG. 1, an endoscope system 10 comprises an endoscope 12, a light source device 14, a processor device 16, a monitor 18, and a user interface 19. The endoscope 12 irradiates a subject, which is an object to be observed, with illumination light and picks up the image of the subject that is irradiated with the illumination light. The light source device 14 generates illumination light with which the subject is to be irradiated. The processor device 16 performs the control of the endoscope system 10, image processing, and the like. The monitor 18 is a display unit that displays an image output from the processor device 16. The user interface 19 is an input device used to perform setting input for the processor device 16 and the like, and includes a keyboard KB, a mouse MS, and the like.

The user interface 19 is not limited to the mouse MS and the keyboard KB, and may be a graphical user interface, voice input, a touch display, or the like. Further, a medical image processing device according to an embodiment of the invention includes an image acquisition unit 54 and an image processing unit 61 (see FIG. 2) that are provided in the processor device 16 and the user interface 19.

The endoscope 12 includes an insertion part 12a that is to be inserted into an object to be examined, an operation part 12b that is provided at the proximal end portion of the insertion part 12a, a bendable part 12c that is provided on the distal end side of the insertion part 12a, and a distal end part 12d. The bendable part 12c is bent by the operation of an angle knob 12e of the operation part 12b. Since the bendable part 12c is bent, the distal end part 12d faces in a desired direction. The distal end part 12d is provided with a jet port (not shown) that jets air, water, or the like toward a subject.

Further, the operation part 12b is provided with a zoom operation part 13 in addition to the angle knob 12e. The image of a subject can be picked while being enlarged or reduced in size by the operation of the zoom operation part 13. Furthermore, a forceps channel (not shown) into which a treatment tool or the like is to be inserted is provided over the distal end part 12d from the insertion part 12a. The treatment tool is inserted into the forceps channel through a forceps inlet 12f.

Figure 2:
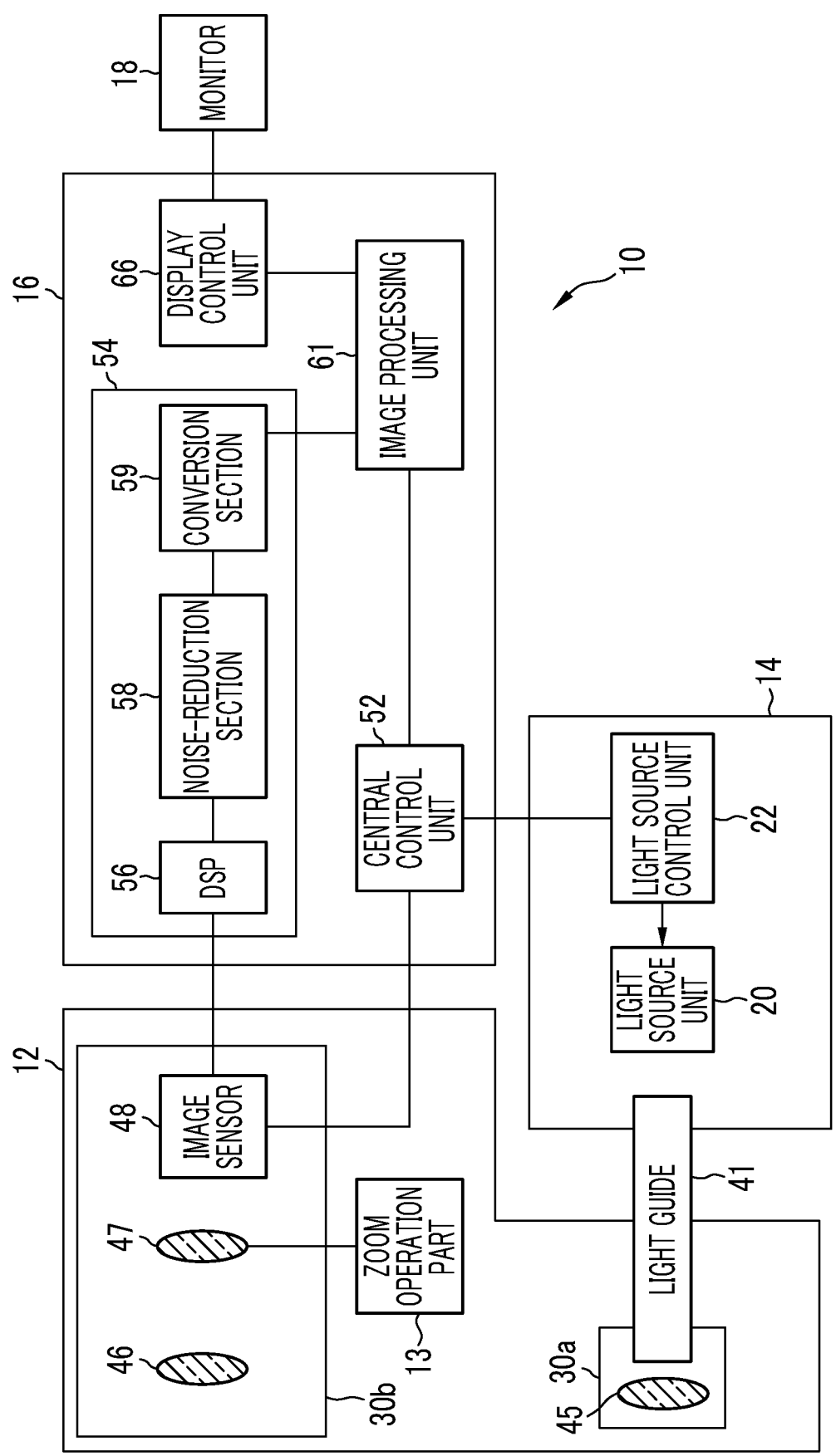
FIG. 2 is a block diagram of the endoscope system.

As shown in FIG. 2, the light source device 14 comprises a light source unit 20 and a light source control unit 22. The light source unit 20 emits illumination light for illuminating a subject. The light source unit 20 comprises one or a plurality of light sources. The light source control unit 22 controls the drive of the light source unit 20. The light source control unit 22 independently controls the timing of the turn-on or turn-off of the light source of the light source unit 20, the amount of light to be emitted at the time of turn-on, and the like. As a result, the light source unit 20 can emit a plurality of kinds of illumination light of which the amounts of light to be emitted or light emission timings are different from each other.

The illumination light emitted from the light source unit 20 is incident on a light guide 41. The light guide 41 is built in the endoscope 12 and a universal cord (not shown), and transmits the illumination light to the distal end part 12d of the endoscope 12. The universal cord is a cord that connects the endoscope 12 to the light source device 14 and the processor device 16. A multimode fiber can be used as the light guide 41. For example, a thin fiber cable of which a total diameter of a core diameter of 105 μm, a cladding diameter of 125 μm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and illumination light is emitted to a subject through the illumination lens 45. The image pickup optical system 30b includes an objective lens 46, a zoom lens 47, and an image sensor 48. The image sensor 48 picks up the image of the subject by using the reflected light of the illumination light, which returns from the subject through the objective lens 46 and the zoom lens 47, and the like (including scattered light, fluorescence emitted from the subject, fluorescence caused by a medicine administered to the subject, and the like in addition to the reflected light). The zoom lens 47 is moved by the operation of the zoom operation part 13, and enlarges or reduces the image of the subject to be picked up by the image sensor 48.

The image sensor 48 is a color sensor including, for example, primary color filters, and comprises three kinds of pixels of B pixels (blue pixels) including blue color filters, G pixels (green pixels) including green color filters, and R pixels (red pixels) including red color filters. The blue color filter mainly transmits violet to blue light. The green color filter mainly transmits green light, and the red color filter mainly transmits red light. In a case where the image of a subject is picked up using the primary color image sensor 48 as described above, a maximum of three kinds of images of a B image (blue image) obtained from the B pixels, a G image (green image) obtained from the G pixels, and an R image (red image) obtained from the R pixels can be obtained at the same time.

A charge coupled device (CCD) sensor or a complementary metal oxide semiconductor (CMOS) sensor can be used as the image sensor 48. Further, the image sensor 48 of this embodiment is a primary color sensor, but a complementary color sensor can also be used. A complementary color sensor includes, for example, cyan pixels including cyan color filters, magenta pixels including magenta color filters, yellow pixels including yellow color filters, and green pixels including green color filters. In a case where a complementary color sensor is used, images obtained from the respective color pixels can be converted into a B image, a G image, and an R image through complementary color-primary color conversion. Further, a monochrome sensor, which includes no color filter, can be used as the image sensor 48 instead of a color sensor. In this case, the images of a subject are sequentially picked up using illumination lights having the respective colors, such as B, G, and R, so that images having the respective colors can be obtained.

The processor device 16 includes a central control unit 52, an image acquisition unit 54, an image processing unit 61, and a display control unit 66. The central control unit 52 performs the general control of the endoscope system 10, such as the synchronization control of the irradiation timing of illumination light and an image pickup timing. Further, in a case where various kinds of settings are input using the user interface 19 or the like, the central control unit 52 inputs the input various kind of settings to each part of the endoscope system 10, such as the light source control unit 22, the image sensor 48, or the image processing unit 61.

The image acquisition unit 54 acquires the picked-up image of the subject from the image sensor 48. Since the image acquired by the image acquisition unit 54 is an image obtained by a medical device, such as the endoscope 12, the image acquired by the image acquisition unit 54 is referred to as a medical image. The image acquisition unit 54 includes a digital signal processor (DSP) 56, a noise-reduction section 58, and a conversion section 59, and performs various kinds of processing on the acquired medical image as necessary by using these. The DSP 56 performs various kinds of processing, such as defect correction processing, offset processing, gain correction processing, linear matrix processing, gamma conversion processing, demosaicing, and YC conversion processing, on the acquired medical image as necessary.

The defect correction processing is processing for correcting the pixel value of a pixel corresponding to a defective pixel of the image sensor 48. The offset processing is processing for reducing a dark current component from the image having been subjected to the defect correction processing and setting an accurate zero level. The gain correction processing is processing for adjusting the signal level of each image by multiplying the image, which has been subjected to the offset processing, and a gain together. The linear matrix processing is processing for improving the color reproducibility of the image subjected to the offset processing, and the gamma conversion processing is processing for adjusting the brightness or chroma of the image having been subjected to the linear matrix processing.

The demosaicing is performed in a case where the image sensor 48 is a color sensor. The demosaicing (also referred to as equalization processing or demosaicing processing) is processing for interpolating the pixel value of a missing pixel, and is performed on the image having been subjected to the gamma conversion processing. The missing pixel is a pixel that does not have a pixel value due to the arrangement of color filters (since pixels having other colors are disposed in the image sensor 48). For example, since a B image is an image that is obtained from the image pickup of a subject at B pixels, pixels of the B image, which are present at positions corresponding to the G pixels and the R pixels, do not have a pixel value. In the demosaicing, the pixel values of pixels of a B image, which are present at positions corresponding to the G pixels and the R pixels of the image sensor 48, are generated through the interpolation of the B image. The YC conversion processing is processing for converting the image, which has been subjected to the demosaicing, into luminance channels Y, color-difference channels Cb, and color-difference channels Cr.

The noise-reduction section 58 performs noise-reduction processing on the luminance channels Y, the color-difference channels Cb, and the color-difference channels Cr by using, for example, a moving-average method, a median filter method, or the like. The conversion section 59 converts the luminance channels Y, the color-difference channels Cb, and the color-difference channels Cr, which have been subjected to the noise-reduction processing, into an image having the respective colors of BGR again.

The image processing unit 61 performs various kinds of image processing on the medical image that is acquired by the image acquisition unit 54. Further, the image processing unit 61 extracts a region of interest from the medical image, and calculates diagnosis support information, which is used to support the diagnosis of an object to be observed, from the extracted region of interest. The extraction of the region of interest and the calculation of the diagnosis support information will be described later. The display control unit 66 converts the medical image or the diagnosis support information, which are sent from the image processing unit 61, into a format suitable to be displayed on the monitor 18, and outputs the medical image or the converted diagnosis support information to the monitor 18. Accordingly, at least one of the medical image or the diagnosis support information is displayed on the monitor 18.

Figure 3:
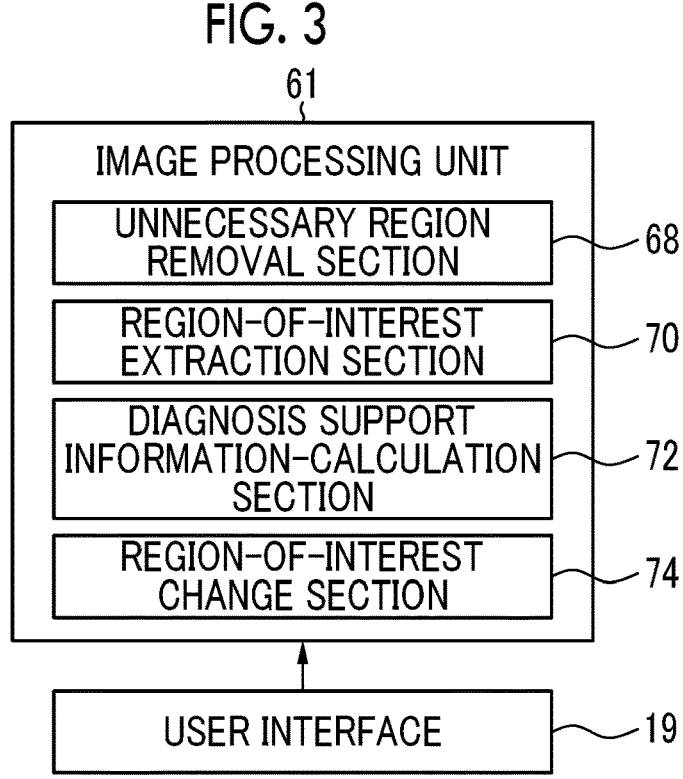
FIG. 3 is a block diagram showing the functions of an image processing unit of a first embodiment.

As shown in FIG. 3, the image processing unit 61 comprises an unnecessary region removal section 68, a region-of-interest extraction section 70, a diagnosis support information-calculation section 72, and a region-of-interest change section 74. The unnecessary region removal section 68 performs removal processing for removing excessively dark regions and excessively bright regions, which obstruct the accurate calculation of the diagnosis support information, from the medical image. In this removal processing, a lower limit and an upper limit are set for each of the B image, the G image, and the R image of the medical image. Further, a region of which the brightness is lower than the lower limit is detected as an excessively dark region, and is removed from each image. Likewise, a region of which the brightness is higher than the upper limit is detected as an excessively bright region, and is removed from each image. A region of interest is extracted from the medical image from which the excessively dark regions and the excessively bright regions have been removed. The excessively dark regions and the excessively bright regions may not be removed depending on the state of the medical image.

The region-of-interest extraction section 70 detects a region of interest, which is to be noticed as an object to be examined or diagnosed, from the medical image. The region-of-interest extraction section 70 calculates a first feature quantity from the medical image. Then, a region where the calculated first feature quantity is in a first region extraction range is extracted as a region of interest. The first region extraction range represents the numerical range of the first feature quantity that is set in advance to extract a region of interest. For example, the region-of-interest extraction section calculates "ln(G/B)", which is obtained from the logarithmic transformation of B/G denoting a ratio of a B image to a G image, as the first feature quantity and extracts a region where "ln(G/B)" is in the first region extraction range as a region of interest. The region of a superficial blood vessel is mainly included in the region of interest that is extracted on the basis of the first feature quantity. The region of interest, which is extracted by the region-of-interest extraction section 70, is not limited to a two-dimensional region, such as the surface of an object to be observed. For example, a three-dimensional region in a depth direction (infiltration) of an object to be observed may be extracted as a region of interest in addition to the surface of an object to be observed.

Here, a blood vessel index value about a blood vessel or a glandular index value about a glandular structure to be described later may be used other than "ln(G/B)" as the first feature quantity. For example, the region-of-interest extraction section 70 may use feature quantities, which are obtained from not only a convolutional neural network performed on the medical image but also the color information of the medical image, the gradient of pixel values, and the like, as the first feature quantity. The gradient of pixel values, and the like are changed depending on, for example, the shape (the overall undulation or the local recess or protuberance of a mucous membrane, or the like), the color (a color, such as whitening caused by inflammation, bleeding, redness, or atrophy), the characteristics of a tissue (the thickness, the depth, or the density of a blood vessel, a combination thereof, or the like), the characteristics of structure (a pit pattern, and the like), or the like of a subject.

Further, the region of interest, which is extracted by the region-of-interest extraction section 70, is a region including, for example, a lesion part typified by a cancer, a benign tumor, an inflamed part (including a part where a change, such as bleeding or atrophy, occurs in addition to so-called inflammation), a cautery mark caused by heating or a marking portion marked by coloration using a colorant, a fluorescent agent, or the like, or a biopsy portion where biopsy is performed. That is, a region including a lesion; a region where a lesion is likely to occur; a region that has been subjected to certain treatment, such as biopsy; a treatment tool, such as a clip or forceps; a region where detailed observation is needed regardless of the possibility of a lesion, such as a dark region (a region where observation light does not easily reach since the region is positioned on the back of a fold or in a lumen); or the like may be the region of interest. In the endoscope system 10, the region-of-interest extraction section 70 detects a region, which includes at least one of the lesion part, the benign tumor, the inflamed part, the marking portion, or the biopsy portion, as the region of interest.

Figure 4:
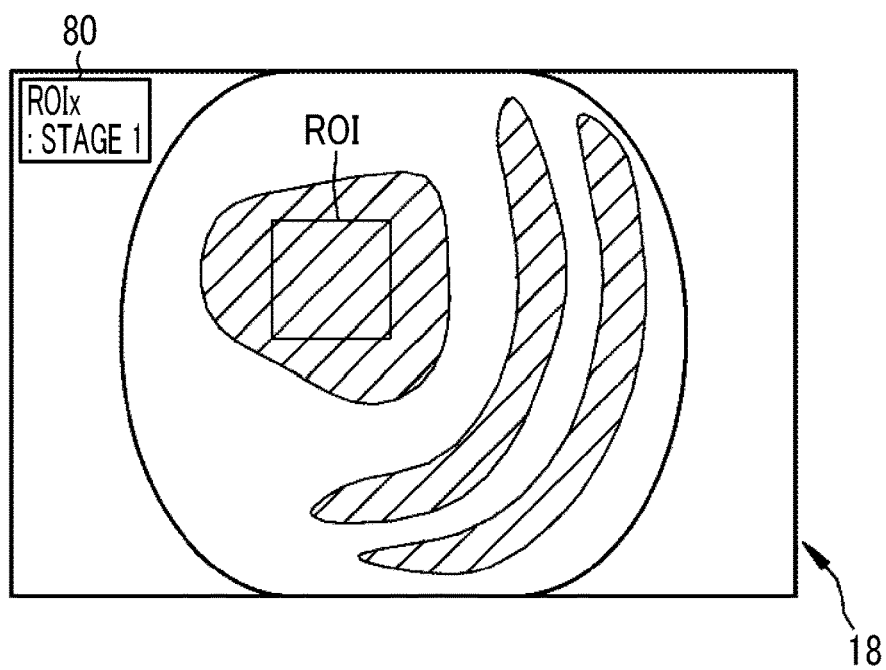
FIG. 4 is an image diagram showing a region of interest and diagnosis support information of the first embodiment.

The diagnosis support information-calculation section 72 calculates various index values from the region of interest extracted by the region-of-interest extraction section 70, and calculates diagnosis support information, which is used to support the diagnosis of a lesion part, on the basis of the various index values having been calculated. Blood vessel index values about a blood vessel, such as vascular density and the travel pattern of blood vessels, a glandular index value about a glandular structure, and the like are included in the various index values. Examples of the diagnosis support information include the degree of progress (stage) of a lesion part, and the like. The calculated diagnosis support information 80 is displayed on the monitor 18 in association with the region of interest ROI as shown in FIG. 4 ("stage 1" in FIG. 4).

The region-of-interest change section 74 performs correction processing for correcting the region of interest, which is extracted by the region-of-interest extraction section 70, to a second region of interest from a first region of interest. The first region of interest is a region of interest that is not yet subjected to the correction processing, and the second region of interest is a region of interest that has been subjected to the correction processing. The correction processing is performed in a case where the user interface 19 receives an instruction of the correction processing that is one of instructions to be given to the region-of-interest change section 74. It is preferable that the mouse MS is used as the user interface 19 in the first embodiment. The enlargement, the reduction, or the position change of the first region of interest is included in the correction processing. After the correction processing, the diagnosis support information-calculation section 72 recalculates various index values from the second region of interest and recalculate diagnosis support information, which is used to support the diagnosis of a lesion part, on the basis of the various index values having been calculated. After the correction processing, information about the correction processing may be stored as region correction information in a region correction information-storage section 76 (see FIG. 13) to be described later.

Figure 5:
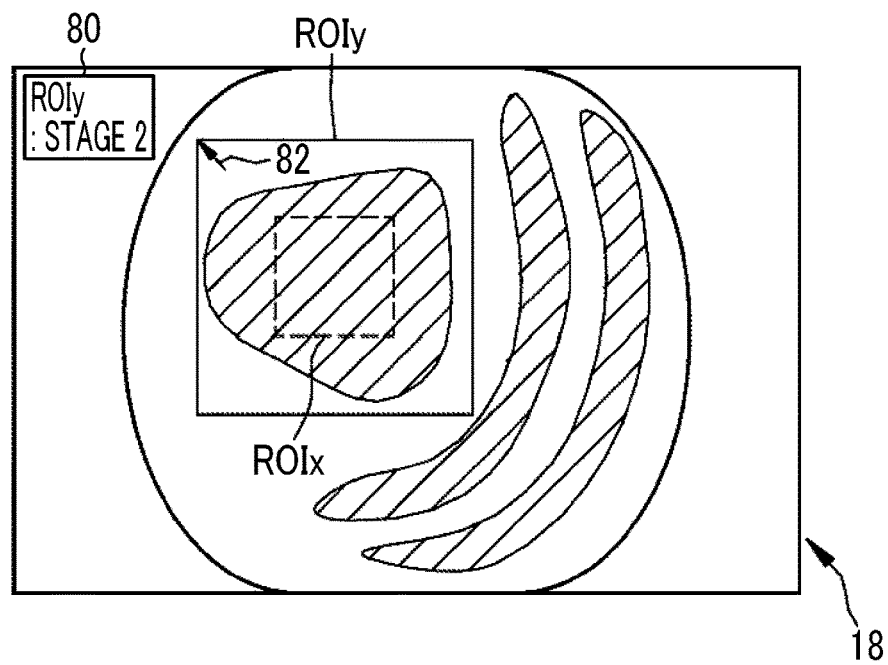
FIG. 5 is a diagram illustrating a second region of interest ROIy that is an enlarged first region of interest ROIx.

In a case where a user is to perform the enlargement of the first region of interest of the correction processing, the user operates the mouse MS to position a pointer 82 displayed on the monitor 18 to a boundary portion of the first region of interest ROIx (shown by a dotted line) as shown in FIG. 5. Then, the user operates the mouse MS so that the pointer 82 is moved in a direction where the first region of interest ROIx is enlarged in a state where the user clicks the right button of the mouse MS at the boundary portion of the first region of interest ROIx. Accordingly, the second region of interest ROIy (shown by a solid line), which is an enlarged first region of interest ROIx, is obtained. Then, diagnosis support information 80 is recalculated from the second region of interest ROIy after the enlargement, and the recalculated diagnosis support information 80 is displayed on the monitor 18 in association with the second region of interest ROIy (the recalculated diagnosis support information is "stage 2"). On the other hand, in a case where the user is to reduce the first region of interest ROIx in size, the user operates the mouse MS so that the pointer 82 is moved in a direction where the first region of interest ROIx is reduced in size in a state where the user clicks the right button of the mouse MS at the boundary portion of the first region of interest ROIx.

Figure 6:
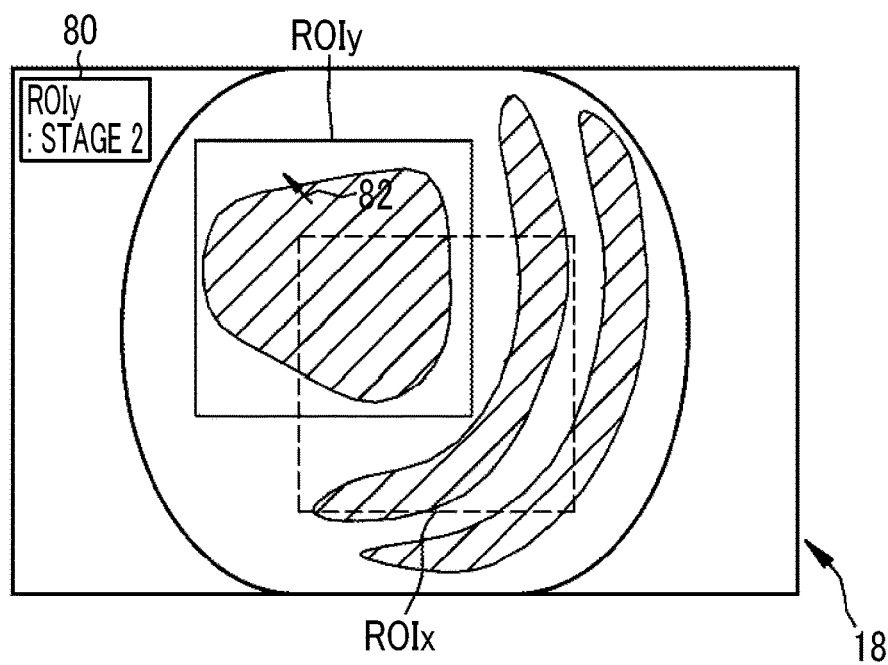
FIG. 6 is a diagram illustrating the second region of interest ROIy in a case where the position of the first region of interest ROIx is changed.

In a case where the user is to perform the position change of the first region of interest of the correction processing, the user operates the mouse MS to set the pointer 82 in the first region of interest ROIx (shown by a dotted line) as shown in FIG. 6. Then, the user operates the mouse MS so that the pointer 82 is moved toward a region to which the user wants to move the position of the first region of interest in a state where the user clicks the right button of the mouse MS in the first region of interest ROIx. Accordingly, the second region of interest ROIy (shown by a solid line), which has been subjected to the position change of the first region of interest ROIx, is obtained. Diagnosis support information is recalculated from the second region of interest ROIy after the position change, and the recalculated diagnosis support information is displayed on the monitor 18 in association with the second region of interest ROIy (the recalculated diagnosis support information is "stage 2").

Figure 7:
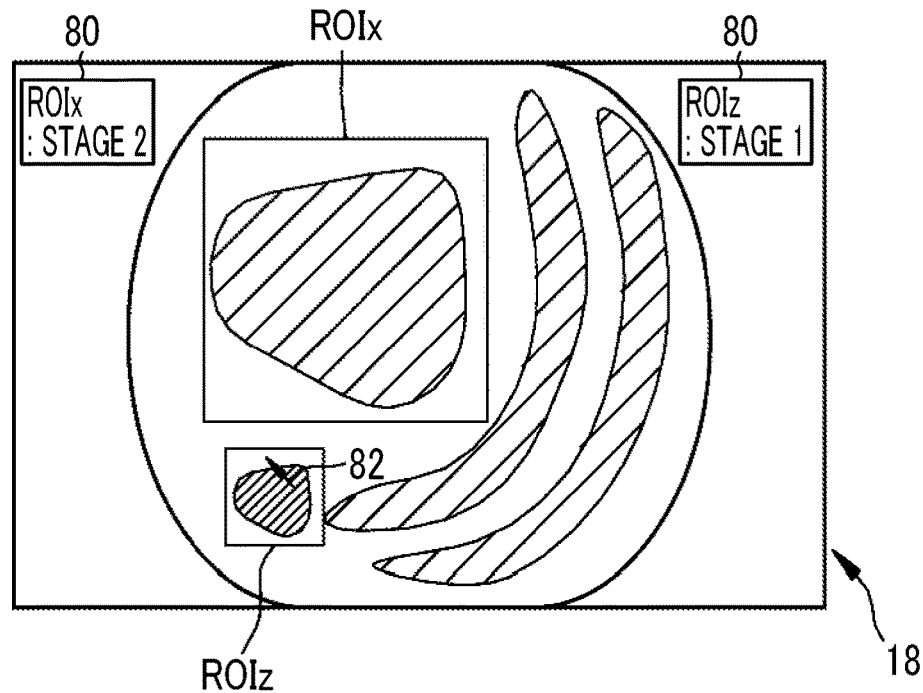
FIG. 7 is a diagram illustrating a third region of interest ROIz that is newly added.

Further, the region-of-interest change section 74 may perform addition processing for adding a third region of interest to a position, which is different from the position of the first region of interest, in addition to the first region of interest as the region of interest that is extracted by the region-of-interest extraction section 70. In the addition processing, the user operates the mouse MS so that the pointer 82 is set in a region where the user wants to newly set a region of interest as shown in FIG. 7. In a case where the pointer 82 is set at a portion where the user wants to set a region of interest, the user clicks the left button of the mouse MS. Accordingly, a third region of interest ROIz is added to a position that is different from the position of the first region of interest ROIx. It is preferable that the third region of interest ROIz to be added is a square region. Diagnosis support information is recalculated from the third region of interest ROIz after the addition, and the recalculated diagnosis support information is displayed on the monitor 18 in association with the third region of interest ROIz (the diagnosis support information of the first region of interest ROIx is "stage 2" and the diagnosis support information of the third region of interest ROIz is "stage 1"). The added third region of interest ROIz can also be subjected to correction processing, such as enlargement, reduction, or position change.

Figure 8:
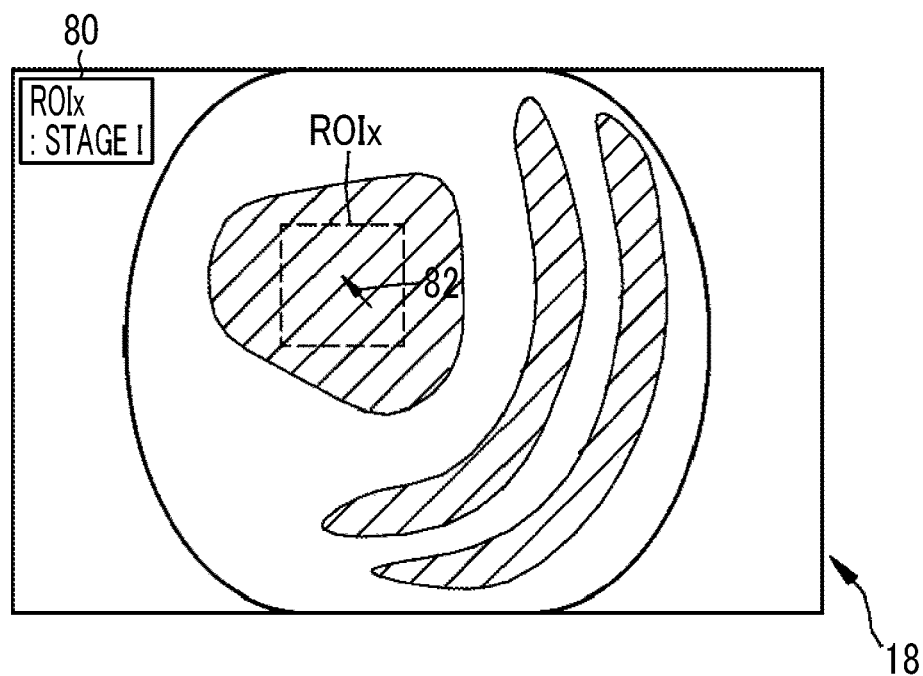
FIG. 8 is a diagram illustrating deletion processing.

Furthermore, the region-of-interest change section 74 may perform deletion processing for deleting the first region of interest as the region of interest that is extracted by the region-of-interest extraction section 70. In the deletion processing, the user operates the mouse MS to set the pointer 82 in the first region of interest ROIx as shown in FIG. 8. Then, the user clicks the right button of the mouse MS a plurality of times (for example, two times) in the first region of interest ROIx. Accordingly, the first region of interest ROIx is deleted. Moreover, the diagnosis support information displayed in association with the first region of interest ROIx is also deleted (a dotted line in FIG. 8 shows that the diagnosis support information is deleted). In a case where a plurality of regions of interest are displayed on the monitor 18 as in a fourth embodiment or a fifth embodiment to be described later, unnecessary regions of interest of the plurality of regions of interest may be deleted by the deletion processing.

Figure 9:
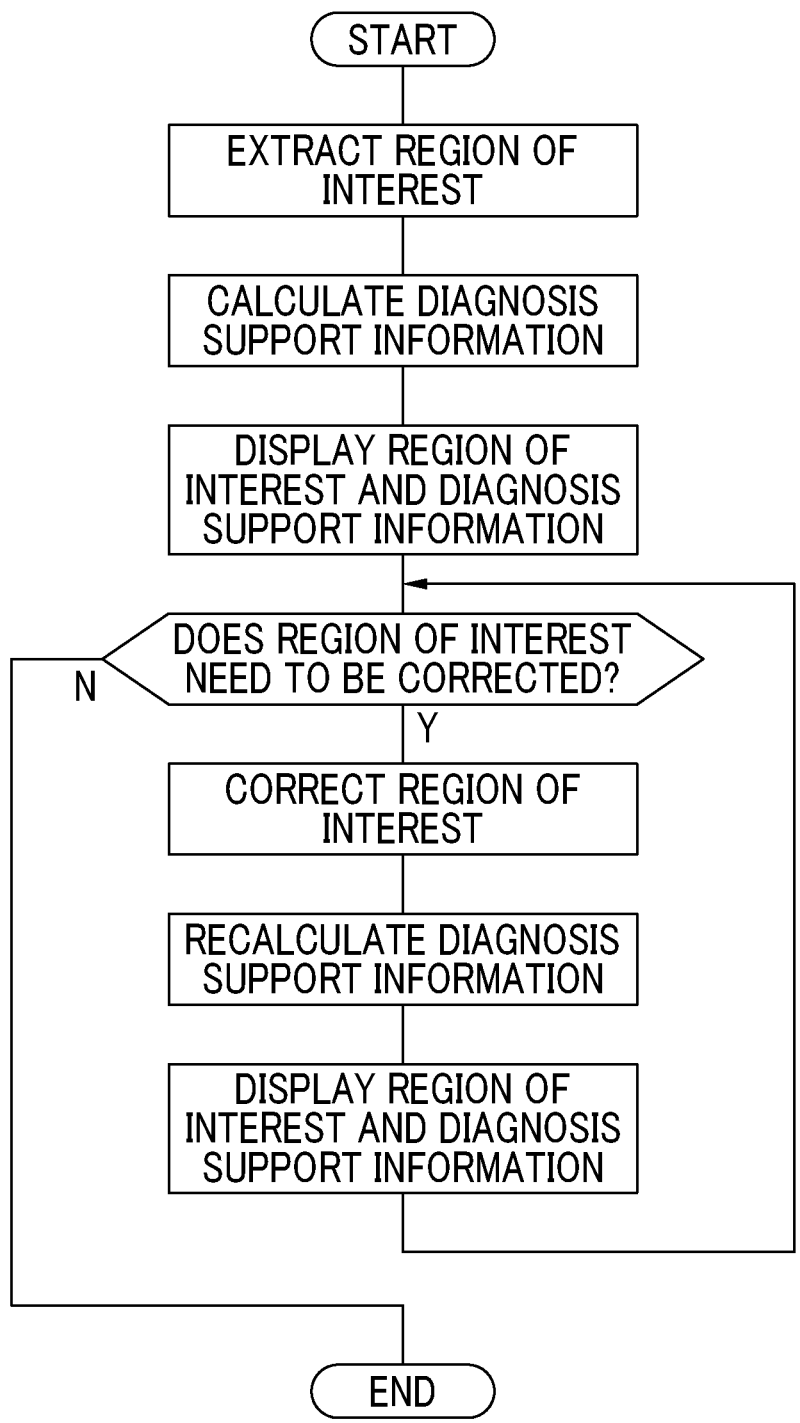
FIG. 9 is a flowchart showing the flow of correction processing.

Next, the correction processing for correcting a region of interest will be described with reference to a flowchart shown in FIG. 9. First, a first feature quantity is calculated from an acquired medical image, and a region of interest is extracted on the basis of the calculated first feature quantity. Then, diagnosis support information is calculated from the region of interest. The region of interest and the diagnosis support information are displayed on the monitor 18. A user checks the region of interest and the diagnosis support information, which are displayed on the monitor 18, to determine whether or not the calculated diagnosis support information is reasonable. As a result, in a case where the user determines that the diagnosis support information is reasonable since there is no problem in the result of extraction of the region of interest, correction processing is not performed.

In contrast, in a case where the user determines that the diagnosis support information is not reasonable since there is a problem in the result of extraction of the region of interest, the user determines that the region of interest needs to be corrected and performs correction processing. In the correction processing, the user corrects a first region of interest having a problem as a region of interest by the user interface 19, such as the mouse MS. Accordingly, a second region of interest, which is the corrected first region of interest, is obtained. After the correction processing, diagnosis support information is recalculated from the second region of interest. The recalculated diagnosis support information is displayed on the monitor 18 together with the second region of interest. The correction of the region of interest and the recalculation of the diagnosis support information are repeatedly performed until the user determines that the region of interest does not need to be corrected.

Second Embodiment

In a second embodiment, correction processing for correcting a first region of interest to a second region of interest is performed by changing a region-of-interest extraction condition for the extraction of a region of interest. Here, the region-of-interest extraction condition is a condition about the first region extraction range described in the first embodiment. A plurality of first region extraction ranges are provided in the second embodiment so that a condition can be changed to a plurality of region-of-interest extraction conditions. Five region extraction ranges R11, R12, R13, R14, and R15 are provided as the plurality of first region extraction ranges. The region extraction range R11 is narrowest, the region extraction ranges R12, R13, and R14 become wider in this order, and the region extraction range R15 is widest. The second embodiment is the same as the first embodiment except that the correction processing is performed by changing the region-of-interest extraction condition.

Figure 10:
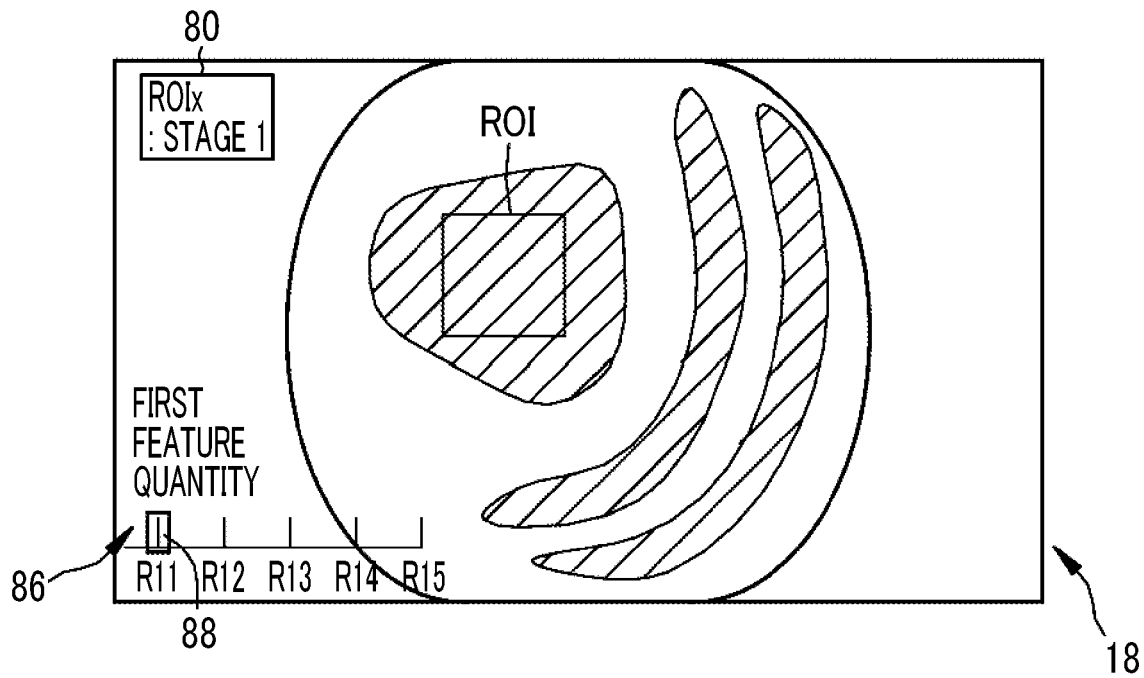
FIG. 10 is an image diagram showing a region of interest, diagnosis support information, and a slider for changing a first region extraction range.

As shown in FIG. 10, the plurality of first region extraction ranges R11, R12, R13, R14, and R15 correspond to gradations R11, R12, R13, R14, and R15 of a slide bar 86 indicating the first region extraction range, respectively. A slider 88 provided on the slide bar 86 indicates a first region extraction range that is currently set. Here, the slider is set to the region extraction range R11. Accordingly, a region where the first feature quantity is in the first region extraction range R11 is extracted as a region of interest ROI, and diagnosis support information 80 is calculated from the region of interest ROI ("stage 1" in FIG. 10).

The slider 88 can be moved on the slide bar 86 in a case where the user interface 19 receives an instruction to change the first region extraction range. Accordingly, the first region extraction range to be used for the extraction of a region of interest can be changed. That is, the region-of-interest extraction condition can be changed. Sliders 92 and 98 to be described later can also be moved by the operation of the user interface 19.

Figure 11:
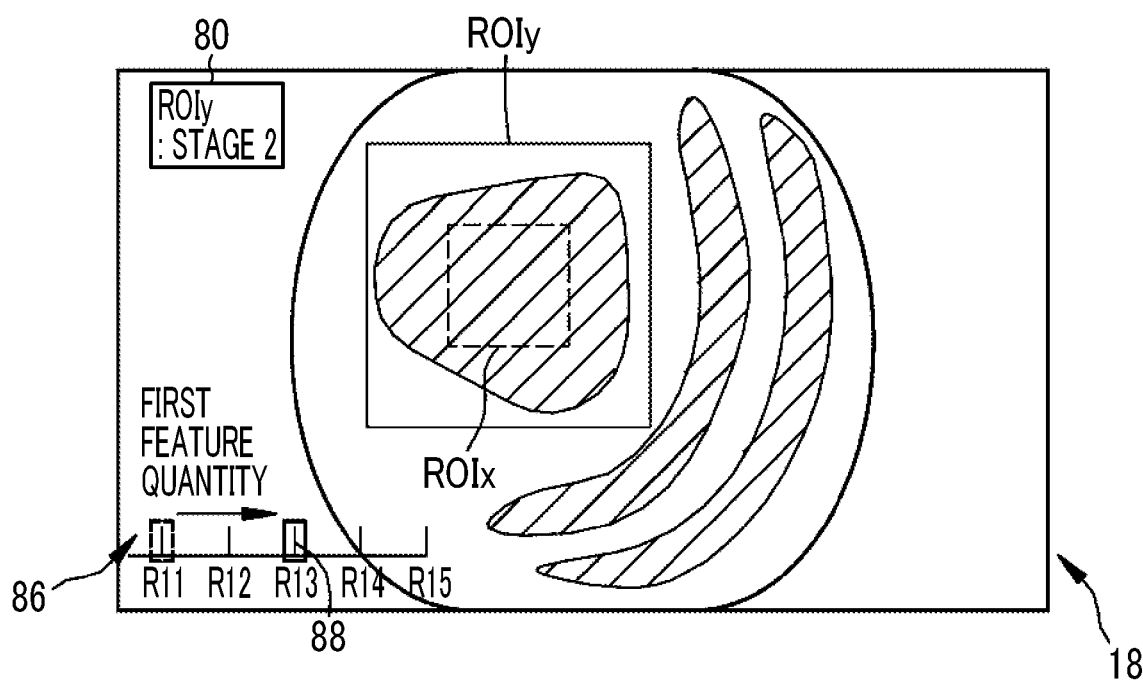
FIG. 11 is a diagram illustrating correction processing that is performed in a second embodiment.

For example, in a case where the slider 88 is set to the gradation R11 before the change of the first region extraction range (shown by a dotted line), a region where the first feature quantity is in the first region extraction range R11 is extracted as a first region of interest ROIx. After the first region of interest is extracted, diagnosis support information is calculated from the first region of interest ROIx and is displayed on the monitor 18. Then, in a case where the slider 88 is moved to the gradation R13 as shown in FIG. 11 (shown by a solid line), a first region extraction range to be used for the extraction of a region of interest is changed to the first region extraction range R13 having a range wider than the first region extraction range R11. Accordingly, a region where the first feature quantity is in the first region extraction range R13 is extracted as a second region of interest ROIy. After the second region of interest is extracted, diagnosis support information 80 is calculated from the second region of interest ROIy and is displayed on the monitor 18 ("stage 2" in FIG. 11).

Figure 12:
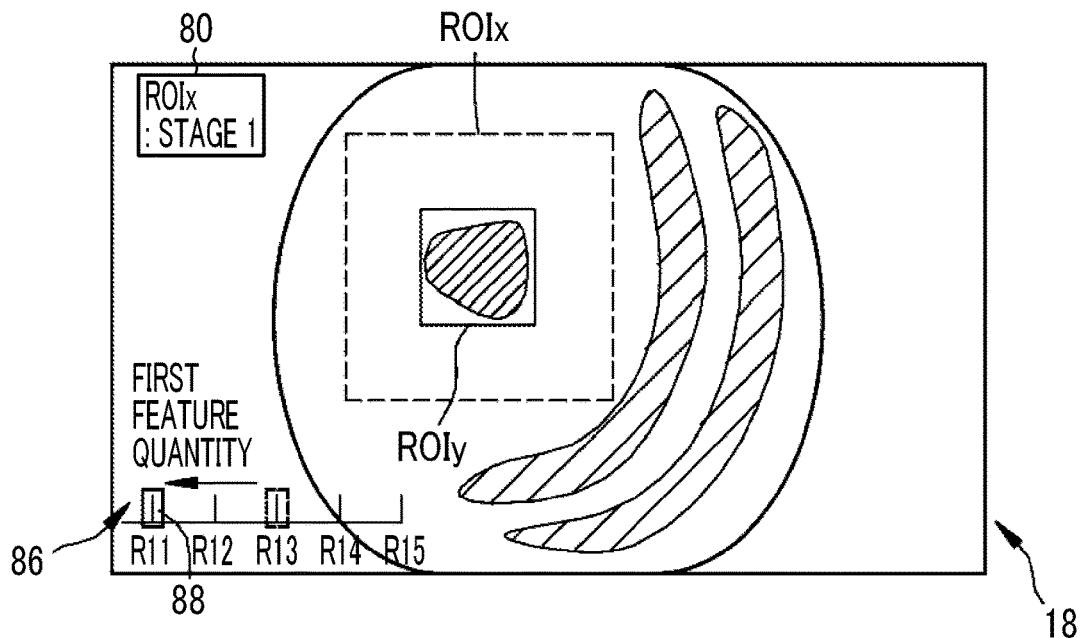
FIG. 12 is a diagram illustrating correction processing that is different from the correction processing of FIG. 11 in the second embodiment.

Further, in a case where the slider 88 is set to the gradation R13 before the change of the first region extraction range (shown by a dotted line), a region where the first feature quantity is in the first region extraction range R13 is extracted as a first region of interest ROIx. After the first region of interest is extracted, diagnosis support information is calculated from the first region of interest ROIx and is displayed on the monitor 18. Then, in a case where the slider 88 is moved to the gradation R11 as shown in FIG. 12 (shown by a solid line), a first region extraction range to be used for the extraction of a region of interest is changed to the first region extraction range R11 having a range narrower than the first region extraction range R13. Accordingly, a region where the first feature quantity is in the first region extraction range R11 is extracted as a second region of interest ROIy. After the second region of interest is extracted, diagnosis support information 80 is calculated from the second region of interest ROIy and is displayed on the monitor 18 ("stage 1" in FIG. 12).

Figure 13:
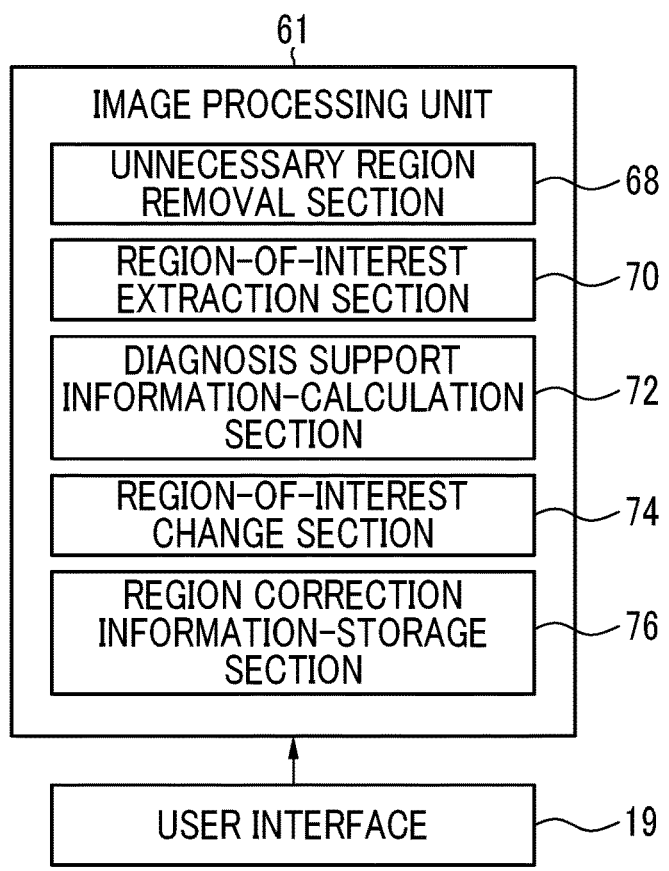
FIG. 13 is a block diagram showing the functions of an image processing unit of the second embodiment.
Figure 14:
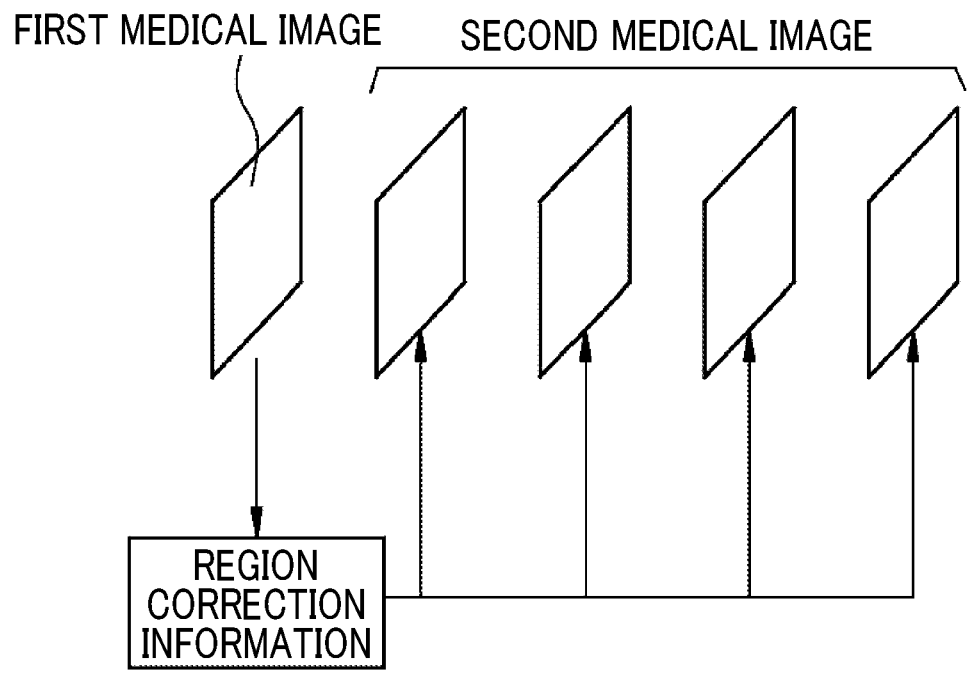
FIG. 14 is a diagram illustrating that the change of a region-of-interest extraction condition performed at the time of acquisition of a first medical image is applied even after the acquisition of a second medical image.

In the second embodiment, the correction history of a region of interest, which is caused by the change of a region-of-interest extraction condition, is stored in the region correction information-storage section 76 shown in FIG. 13 as region correction information. The region correction information is used in a case where a region of interest is extracted from a medical image acquired after the change of a region-of-interest extraction condition. In FIG. 14, region correction information, which is obtained in a first medical image from the change of a region-of-interest extraction condition, is stored in the region correction information-storage section 76. The second medical image is an image that is acquired after the first medical image, and a region of interest is extracted from the second medical image by using the region correction information stored in the region correction information-storage section 76. Even in a third embodiment to be described later, the correction history of a region of interest, which is caused by the change of a region-of-interest extraction condition, may be stored in the region correction information-storage section 76 as region correction information.

For example, in a case where region correction information has the change history of a region extraction range to the first region extraction range R13 from the first region extraction range R11, a region of interest is extracted from the second medical image by using the first region extraction range R13. In a case where region correction information is used as described above, user's effort for the change of a region-of-interest extraction condition, such as the operation of the slider 88, can be saved during diagnosis. Region correction information may be reset by the user interface 19 to return to a default first region extraction range (for example, the first region extraction range R11).

Figure 15:
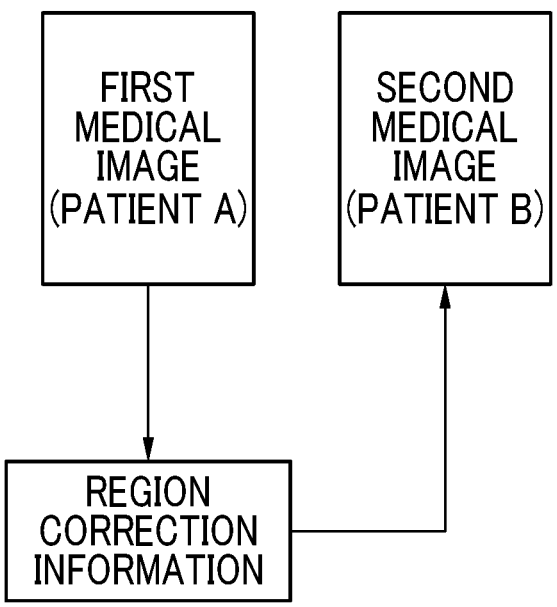
FIG. 15 is a diagram illustrating that the change of a region-of-interest extraction condition performed during the diagnostic imaging of a patient A is also applied to the diagnostic imaging of another patient B.

Further, region correction information may be used in a case where separate patients are diagnosed by the endoscope 12. As shown in FIG. 15, a region of interest is extracted from a first medical image obtained during the diagnostic imaging of a patient A, and the change of a region-of-interest extraction condition performed for the region of interest is stored in the region correction information-storage section 76 as a region correction information. Then, a region of interest is extracted from a second medical image, which is obtained during the diagnostic imaging of a patient B different from the patient A, by using the region correction information stored in the region correction information-storage section 76. The region correction information may be used in a case where diagnostic imaging is performed in another hospital or clinic by using the endoscope 12.

Third Embodiment

In a third embodiment, as in the second embodiment, correction processing for correcting a first region of interest to a second region of interest is performed by changing a region-of-interest extraction condition for the extraction of a region of interest. However, unlike in the second embodiment, a region of interest is extracted using a plurality of feature quantities as the region-of-interest extraction condition. In the third embodiment, a second feature quantity "ln(R/G)" is used in addition to a first feature quantity "ln(G/B)". The second feature quantity "ln(R/G)" is obtained from the logarithmic transformation of a ratio R/G of an R image to a G image. The region of a superficial blood vessel and the region of redness are mainly included in a region of interest that is extracted on the basis of the first feature quantity and the second feature quantity. Since the two first and second feature quantities are used, a condition about a second region extraction range, which represents the numerical range of a second feature quantity set in advance to extract a region of interest, is added to a condition about the first region extraction range, which is described in the first embodiment, as a region-of-interest extraction condition. The third embodiment is the same as the first embodiment except that the correction processing is performed by changing the region-of-interest extraction condition.

Further, a plurality of first region extraction ranges and a plurality of second region extraction ranges are provided so that a condition can be changed to a plurality of region-of-interest extraction conditions. As in the second embodiment, five region extraction ranges R11, R12, R13, R14, and R15 are provided as the plurality of first region extraction ranges. Further, five region extraction ranges R21, R22, R23, R24, and R25 are provided as the plurality of second region extraction ranges. The region extraction range R21 is narrowest, the region extraction ranges R22, R23, and R24 become wider in this order, and the region extraction range R25 is widest.

Figure 16:
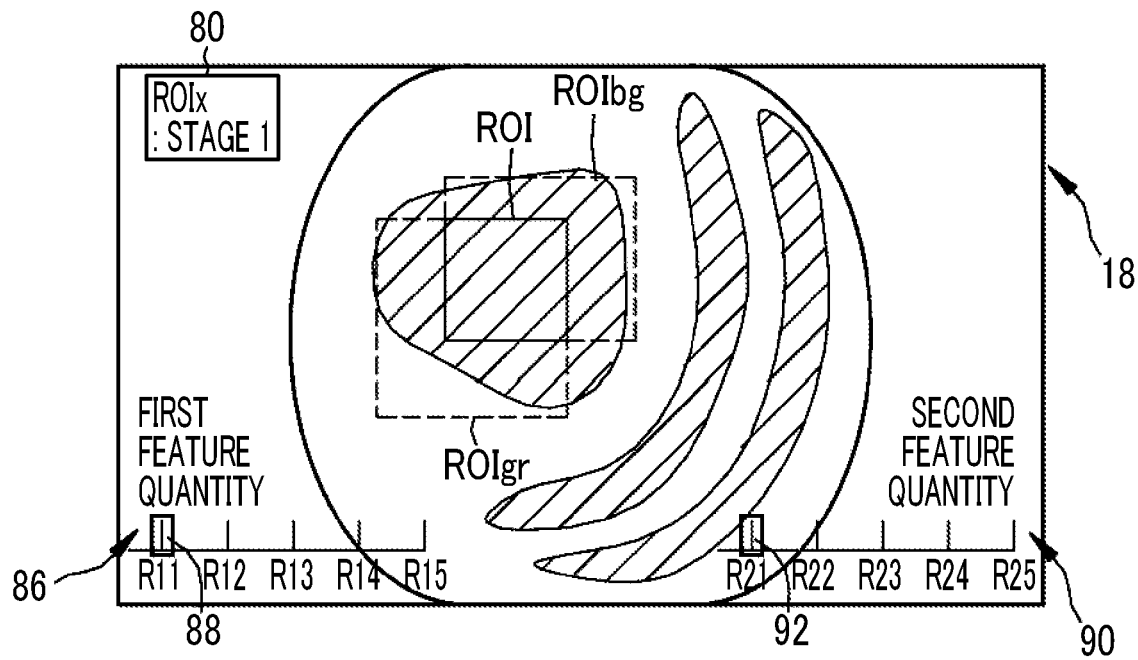
FIG. 16 is an image diagram showing a region of interest, diagnosis support information, a slider for changing a first region extraction range, and a slider for changing a second region extraction range.

As shown in FIG. 16, as in the second embodiment, the plurality of first region extraction ranges R11, R12, R13, R14, and R15 correspond to gradations R11, R12, R13, R14, and R15 of a slide bar 86 indicating the first region extraction range, respectively. Further, the plurality of second region extraction ranges R21, R22, R23, R24, and R25 correspond to gradations R21, R22, R23, R24, and R25 of a slide bar 90 indicating the second region extraction range, respectively. It is possible to change a first region extraction range, which is to be used for the extraction of a region of interest, by moving a slider 88 provided on the slide bar 86. Further, it is possible to change the second region extraction range, which is to be used for the extraction of a region of interest, by moving a slider 92 provided on the slide bar 90.

For example, in a case where the slider 88 is set to the gradation R11 and the slider 92 is set to gradation R21 before the change of the first and second region extraction ranges, a region where a region ROIbg where a first feature quantity is in the first region extraction range R11 and a region ROIgr where the second feature quantity is in the second region extraction range R21 overlap with each other is extracted as the first region of interest ROIx. After the first region of interest is extracted, diagnosis support information 80 is calculated from the first region of interest ROIx and is displayed on the monitor 18 ("stage 1" in FIG. 16).

Figure 17:
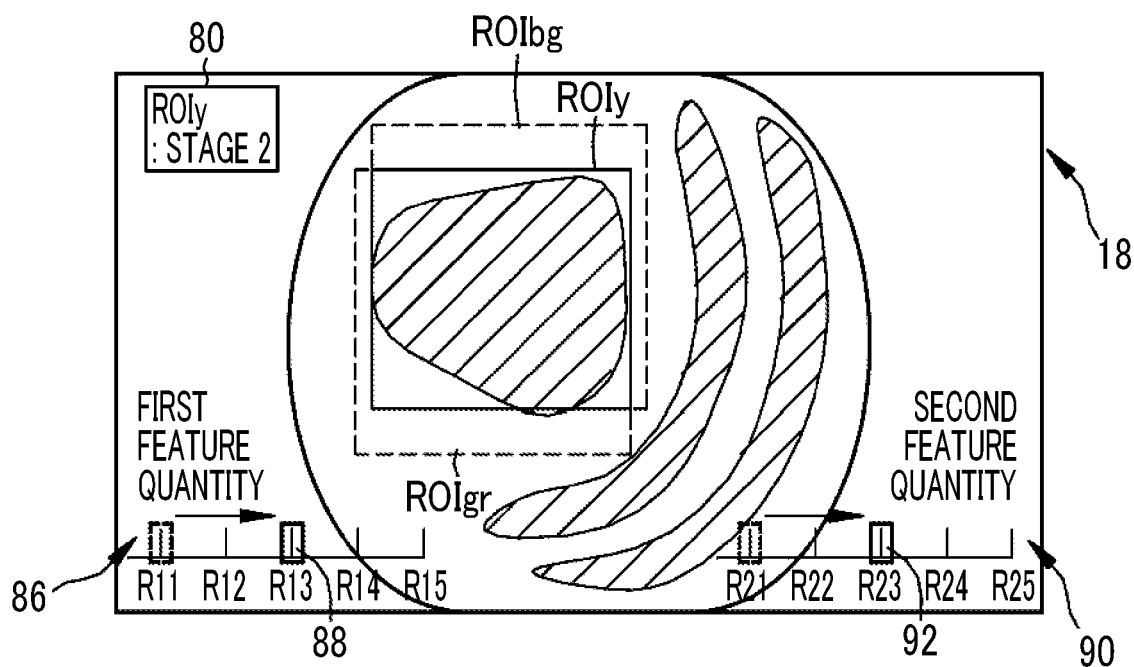
FIG. 17 is a diagram illustrating correction processing of a third embodiment.

Then, in a case where the slider 88 is moved to the gradation R13 as shown in FIG. 17, a first region extraction range to be used for the extraction of a region of interest is changed to the first region extraction range R13 having a range wider than the first region extraction range R11. Further, in a case where the slider 92 is moved to the gradations R23, a second region extraction range to be used for the extraction of a region of interest is changed to the second region extraction range R23 having a range wider than the second region extraction range R21. Accordingly, a region of interest is changed to a second region of interest ROIy where a region ROIbg where a first feature quantity is in the first region extraction range R13 and a region ROIgr where the second feature quantity is in the second region extraction range R23 overlap with each other. After the second region of interest is extracted, diagnosis support information is calculated from the second region of interest ROIy and is displayed on the monitor 18 ("stage 2" in FIG. 17).

In the third embodiment, a region of interest may be extracted using a feature quantity other than the first feature quantity or the second feature quantity. In this case, feature quantity-selection processing for selecting a feature quantity, which is to be used for the extraction of a region of interest, from a plurality of feature quantities may be performed. The feature quantity-selection processing is performed by a feature quantity-selection section 94. The feature quantity-selection section 94 performs feature quantity-selection processing in a case where the user interface 19 receives an instruction for the feature quantity-selection processing.

Figure 19:
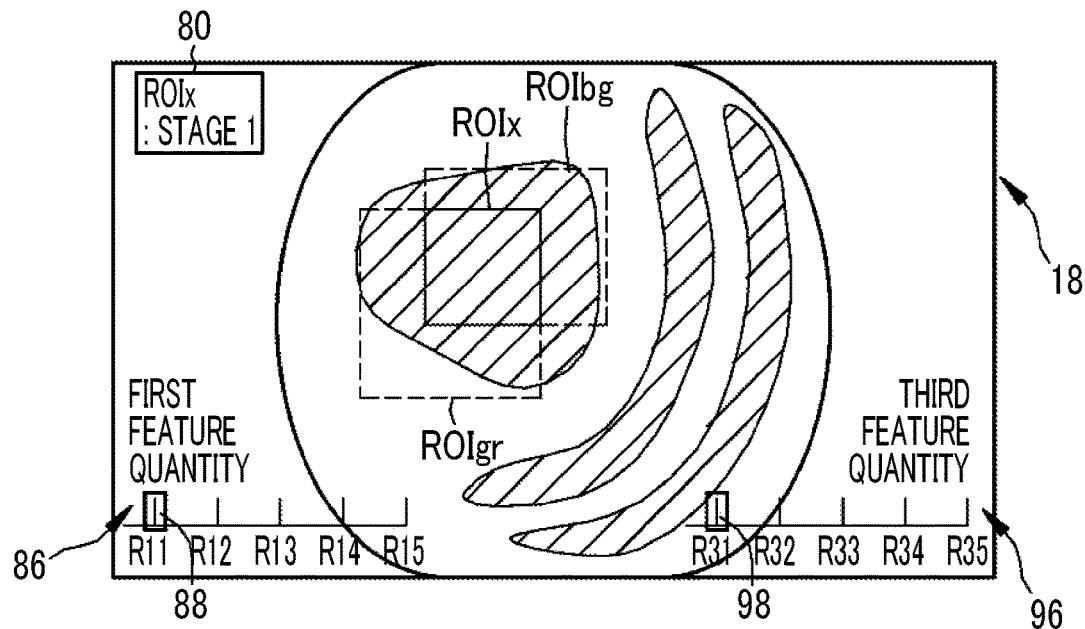
FIG. 19 is an image diagram showing a region of interest, diagnosis support information, a slider for changing a first region extraction range, and a slider for changing a third region extraction range.

For example, in a case where a third feature quantity "ln(B/(R+G+B))" is provided in addition to the first feature quantity "ln(G/B)" and the second feature quantity "ln(R/G)" as a feature quantity to be used for the extraction of a region of interest and the first feature quantity "ln(G/B)" and the third feature quantity "ln(B/(R+G+B))" are selected by the feature quantity-selection section 94, the slide bar 86 and the slider 88 indicating the first feature quantity "ln(G/B)" and a slide bar 96 and a slider 98 indicating the third feature quantity "ln(B/(R+G+B))" are displayed on the monitor 18 as shown in FIG. 19. A plurality of third region extraction ranges R31, R32, R33, R34, and R35, which represent the numerical range of the third feature quantity set in advance to extract a region of interest, correspond to gradations R31, R32, R33, R34, and R35 of the slide bar 96, respectively. It is possible to change the first region extraction range and the third region extraction range, which are to be used for the extraction of a region of interest, by moving the slider 88 and the slider 98.

Fourth Embodiment

In a fourth embodiment, unlike in the first to third embodiments, a plurality of region-of-interest extraction conditions are provided and a plurality of regions of interest are extracted according to the plurality of region-of-interest extraction conditions without correction processing for correcting a first region of interest to a second region of interest. In the fourth embodiment, each region-of-interest extraction condition is a condition about the first region extraction range described in the first embodiment and a plurality of first region extraction ranges are provided. As in the second embodiment, five region extraction ranges R11, R12, R13, R14, and R15 are provided as the plurality of first region extraction ranges. The fourth embodiment is the same as the first embodiment except that a plurality of regions of interest are extracted without correction processing. Further, the number of the region extraction ranges is 5, but may be 5 or less or 5 or more. It is preferable that the number of the region extraction ranges is about 10.

Figure 20:
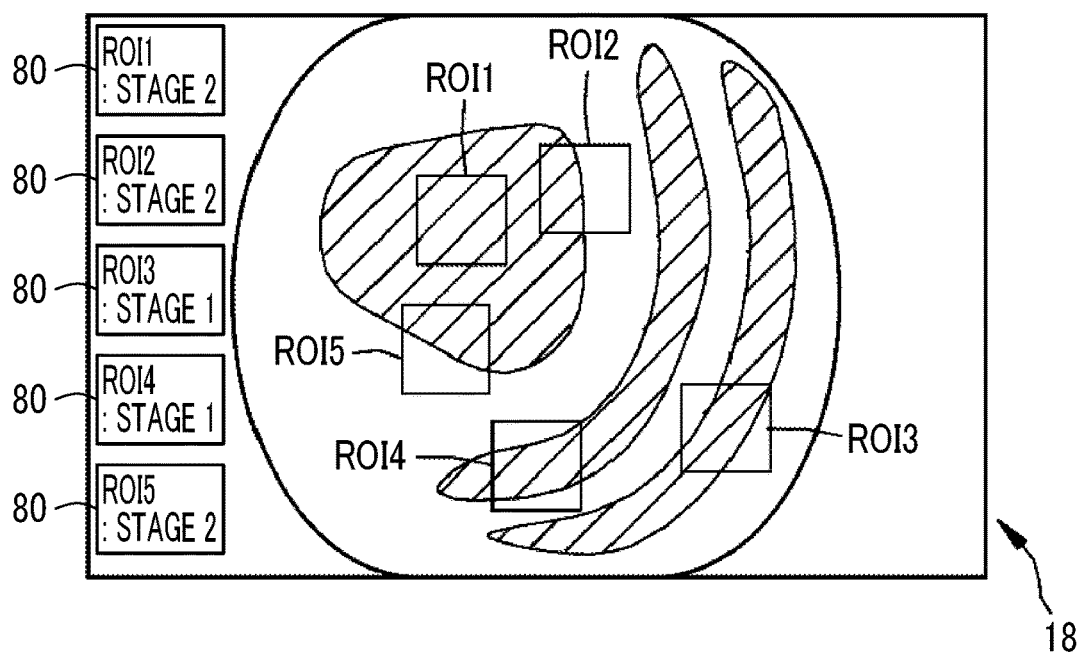
FIG. 20 is an image diagram showing a plurality of regions of interest and diagnosis support information calculated from these regions of interest.

As shown in FIG. 20, a region where the first feature quantity is in the first region extraction range R11 is extracted as region of interest ROI1. Likewise, regions where first feature quantities are in the first region extraction ranges R12, R13, R14, and R15 are extracted as region of interest ROI2, ROI3, ROI4, and ROI5, respectively. Further, diagnosis support information is calculated from each of the extracted regions of interest ROI1 to ROI5 and is displayed on the monitor 18. In FIG. 20, the diagnosis support information 80 of ROI1 is "stage 2", the diagnosis support information 80 of ROI2 is "stage 2", the diagnosis support information 80 of ROI3 is "stage 1", the diagnosis support information 80 of ROI4 is "stage 1", and the diagnosis support information 80 of ROI5 is "stage 2".

It is preferable that brightness or colors corresponding to the respective regions of interest ROI1 to ROI5 are different to allow a user to discriminate the respective regions of interest ROI1 to ROI5. Furthermore, a user may operate the user interface 19 to enlarge and display a specific region of interest among the plurality of regions of interest ROI1 to ROI5. Moreover, it is preferable that the plurality of extracted regions of interest ROI1 to ROI5 are displayed so as to be combined with a medical image together with the diagnosis support information calculated from these regions of interest. It is preferable that the medical image with which the regions of interest are to be combined is a normal light image or a special light image to be described later.

Figure 18:
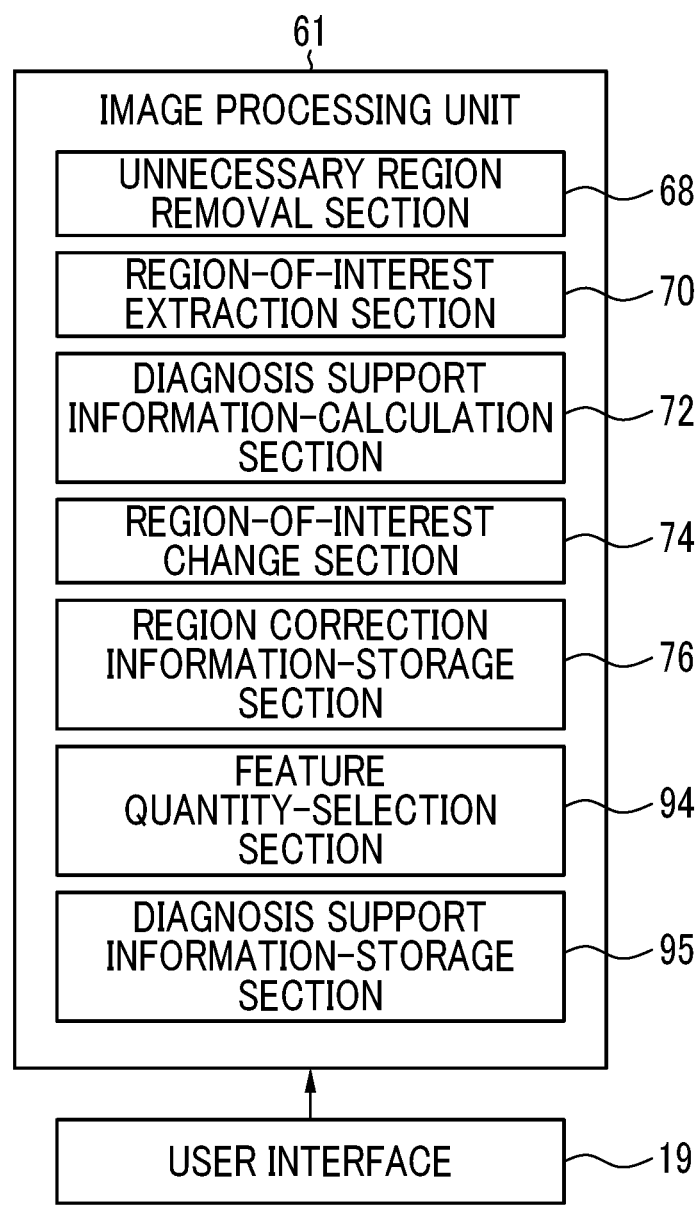
FIG. 18 is a block diagram showing the functions of an image processing unit of the third embodiment.

Further, it is preferable that the medical image from which the plurality of regions of interest ROI1 to ROI5 are extracted and diagnosis support information calculated from these regions of interest are stored in a diagnosis support information-storage section 95 (see FIG. 18) of the processor device 16 in association with each other. The medical image and the diagnosis support information may be stored in association with each other in this way not only in this embodiment but also in the first to third embodiments or the fifth embodiment. In a case where the medical image and the diagnosis support information are to be stored in association with each other and, for example, the diagnosis support information is represented by numerical data, the diagnosis support information may be attached to the header of the medical image so that the diagnosis support information can be read by an image viewer. Furthermore, in a case where the medical image and the diagnosis support information are to be stored, all the diagnosis support information calculated from the plurality of regions of interest ROI1 to ROI5 may be stored or only diagnosis support information selected by a user may be stored. User's selection is performed by the user interface 19.

Fifth Embodiment

In a fifth embodiment, as in the fourth embodiment, a plurality of region-of-interest extraction conditions are provided and a plurality of regions of interest are extracted according to the plurality of region-of-interest extraction conditions without correction processing for correcting a first region of interest to a second region of interest. However, in the fifth embodiment, the region-of-interest extraction conditions are conditions about the first region extraction range described in the first embodiment and conditions about the second region extraction range described in the third embodiment. A plurality of first region extraction ranges are provided and a plurality of second region extraction ranges are also provided. The fifth embodiment is the same as the first embodiment except that a plurality of regions of interest are extracted without correction processing.

As in the second embodiment, five region extraction ranges R11, R12, R13, R14, and R15 are provided as the plurality of first region extraction ranges. Further, as in the third embodiment, five region extraction ranges R21, R22, R23, R24, and R25 are provided as the plurality of second region extraction ranges. The number of the first region extraction ranges is 5, but may be 5 or less or 5 or more. It is preferable that the number of the first region extraction ranges is about 10. The same applies to the second region extraction ranges.

A region where a region where the first feature quantity is in the first region extraction range R11 and a region ROI where the second feature quantity is in the second region extraction range R21 overlap with each other is extracted as a region of interest ROI1. Likewise, a region where a region where the first feature quantity is in the first region extraction range R12 and a region where the second feature quantity is in the second region extraction range R22 overlap with each other is denoted by ROI2. Further, a region where a region where the first feature quantity is in the first region extraction range R13 and a region where the second feature quantity is in the second region extraction range R23 overlap with each other is denoted by ROI3. Furthermore, a region where a region where the first feature quantity is in the first region extraction range R14 and a region where the second feature quantity is in the second region extraction range R24 overlap with each other is denoted by ROI4. Moreover, a region where a region where the first feature quantity is in the first region extraction range R15 and a region where the second feature quantity is in the second region extraction range R25 overlap with each other is denoted by ROI5.

Diagnosis support information is calculated from each of the regions of interest ROI1 to ROI5, which are extracted as described above, and is displayed on the monitor 18 (see FIG. 20). With regard to the respective regions of interest ROI1 to ROI5, regions other than the above-mentioned regions may be used as two regions that are made to overlap with each other for the extraction of these regions of interest ROI1 to ROI5.

The shape of the region of interest ROI is shown as a quadrangular shape (rectangular shape) in the drawings in the first to fifth embodiments, but may be a shape other than a quadrangular shape (rectangular shape). The reason for this is that the shape of a region of interest is changed depending on the distribution state of a feature quantity since the region of interest is extracted on the basis of the feature quantity in the first to fifth embodiments. Further, in a case where the numerical range of a first feature quantity or a second feature quantity for the extraction of a region of interest is changed by correction processing as in the second and third embodiments, there is a case where the shape of the region of interest is changed before and after the correction processing.

In the first to fifth embodiments, examples of a blood vessel index value calculated by the diagnosis support information-calculation section 72 include vascular density and the thickness of a blood vessel, the number of blood vessels, the number of branches, the angle of a branch, a distance between branch points, the number of intersections, a change in thickness, a spacing, a depth from a mucous membrane, a difference in height, an inclination, contrast, a color, a change in color, a meandering degree, the concentration of blood, oxygen saturation, a ratio of arteries, a ratio of veins, the concentration of an administered coloring agent, a travel pattern, a blood flow rate, and the like.

Vascular density is represented by the percentage of blood vessels included in a specific region in an image. The thickness of a blood vessel (the diameter of a blood vessel) is a distance between a blood vessel and the boundary line of a mucous membrane, and is measured by counting, for example, the number of pixels in the lateral direction of a blood vessel from the edge of an extracted blood vessel through the blood vessel. However, the thickness of a blood vessel is the number of pixels, but can be converted into the unit of a length, such as "µm" as necessary in a case where an image pickup distance, zoom magnification, and the like at the time of pickup of a medical image have been already known.

The number of blood vessels is the number of blood vessels that are extracted from the entire medical image or a region of interest. The number of blood vessels is calculated using, for example, the number of branch points of extracted blood vessels (the number of branches), the number of intersections between the extracted blood vessels and other blood vessels (the number of intersections), or the like. The angle of a branch of a blood vessel is an angle between two blood vessels at a branch point. A distance between branch points is a distance in a straight line between any branch point and a branch point next to the branch point or a distance along a blood vessel between any branch point and a branch point next to the branch point.

The number of intersections of blood vessels is the number of intersections where blood vessels having different depths below a mucous membrane intersect with each other in a medical image. More specifically, the number of intersections of blood vessels is the number of intersections where blood vessels present at positions relatively shallow below a mucous membrane intersect with blood vessels present at deep positions.

A change in the thickness of a blood vessel is vascular information about a variation in the thickness of the blood vessel, and is referred to as diameter-nonuniformity. The change in the thickness of the blood vessel is, for example, a ratio of change (referred to as a ratio of increase) in the diameter of the blood vessel. The ratio of change in the diameter of the blood vessel is obtained from "a ratio (%) of change in the diameter of the blood vessel=the minimum diameter/the maximum diameter×100" using the thickness of the thinnest portion (the minimum diameter) of the blood vessel and the thickness of the thickest portion (the maximum diameter) of the blood vessel.

In a case where a medical image obtained from the image pickup of an object to be observed in a past examination and a medical image obtained from the image pickup of the same object to be observed in a subsequent new examination are used, the temporal change of the thickness of the thickness of the same blood vessel extracted from the medical image, which is obtained in the subsequent new examination, from the thickness of a blood vessel extracted from the medical image, which is obtained in the past examination, may be defined as a change in the thickness of the blood vessel.

Further, a ratio of a small-diameter portion or a ratio of a large-diameter portion may be calculated as a change in the thickness of a blood vessel. The small-diameter portion is a portion of which the thickness is equal to or smaller than a threshold value, and the large-diameter portion is a portion of which the thickness is equal to or larger than a threshold value. The ratio of the small-diameter portion is obtained from "the ratio (%) of the small-diameter portion=the length of the small-diameter portion/the length of the blood vessel× 100". Likewise, the ratio of the large-diameter portion is obtained from "the ratio (%) of the large-diameter portion=the length of the large-diameter portion/the length of the blood vessel×100".

The complexity of a change in the thickness of a blood vessel (hereinafter, referred to as "the complexity of a change in thickness") is vascular information that represents how complex a change in the thickness of the blood vessel is in a case where the thickness of the blood vessel is changed, and is vascular information that is calculated from the combination of a plurality of pieces of vascular information representing a change in the thickness of the blood vessel (that is, a ratio of change in the diameter of the blood vessel, a ratio of the small-diameter portion, or a ratio of the large-diameter portion). The complexity of a change in thickness can be obtained from, for example, the product of a ratio of change in the diameter of the blood vessel and a ratio of the small-diameter portion.

The length of a blood vessel is the number of pixels that is counted in the longitudinal direction of an extracted blood vessel.

A spacing between blood vessels is the number of pixels that represent a mucous membrane positioned between the edges of extracted blood vessels. In a case where there is one extracted blood vessel, a spacing between blood vessels does not have a value.

The depth of a blood vessel is measured from a mucous membrane (more specifically, the surface of a mucous membrane). The depth of the blood vessel from the mucous membrane can be calculated on the basis of, for example, the color of the blood vessel. In the case of a special observation image, a blood vessel present at a position close to the surface of the mucous membrane is represented by a magenta color and a blood vessel present at a deep position, which is far from the surface of the mucous membrane below the mucous membrane, is represented by a cyan color. Accordingly, the depth of the blood vessel from the mucous membrane is calculated for each pixel on the basis of the balance of signals corresponding to the respective colors of R, G, and B of pixels extracted as the blood vessel.

A difference in the height of a blood vessel is the magnitude of a difference in the depth of a blood vessel. For example, a difference in the height of one blood vessel to be noticed is obtained from a difference between the depth of the deepest portion (the maximum depth) of the blood vessel and the depth of the shallowest portion (the minimum depth). In a case where a depth is constant, a difference in height is zero.

The inclination of a blood vessel is a ratio of change in the depth of the blood vessel, and is calculated using the length of the blood vessel and the depth of the blood vessel. That is, the inclination of the blood vessel is obtained from "the inclination of the blood vessel=the depth of the blood vessel/the length of the blood vessel". The blood vessel is divided into a plurality of sections, and the inclination of the blood vessel may be calculated in each section.

The area of a blood vessel is the number of pixels extracted as the blood vessel or a value proportional to the number of pixels extracted as the blood vessel. The area of the blood vessel is calculated inside a region of interest, outside a region of interest, or over the entire medical image.

The contrast of a blood vessel is the contrast of an object to be observed relative to a mucous membrane. The contrast of a blood vessel is calculated from, for example, "$Y_V/Y_M$" or "$(Y_V-Y_M)/(Y_V+Y_M)$" using the luminance $Y_V$ of the blood vessel and the luminance $Y_M$ of a mucous membrane.

The color of a blood vessel is each of values of R, G, and B of pixels representing the blood vessel. Further, a change in the color of the blood vessel is a difference or a ratio between the maximum value and the minimum value of each of values of R, G, and B of pixels representing the blood vessel. For example, a ratio between the maximum value and the minimum value of the pixel values of B pixels representing a blood vessel, a ratio between the maximum value and the minimum value of the pixel values of G pixels, or a ratio between the maximum value and the minimum value of the pixel values of R pixels represents a change in the color of the blood vessel. Of course, the color of the blood vessel may be converted into a complementary color, and the color of the blood vessel and a change in the color of the blood vessel may be calculated for each of values of cyan, magenta, yellow, green, and the like.

The meandering degree of a blood vessel is vascular information representing the area of a range where the blood vessel travels while meandering. The meandering degree of the blood vessel is, for example, the minimum rectangular area (the number of pixels) that includes a blood vessel of which the meandering degree is to be calculated. Further, a ratio of the length of a blood vessel to a distance in a straight line between the starting point and the end point of the blood vessel may be used as the meandering degree of the blood vessel.

The concentration of blood in a blood vessel is vascular information proportional to the amount of hemoglobin included in the blood vessel. Since a ratio (G/R) of the pixel value of a G pixel to the pixel value of an R pixel representing a blood vessel is proportional to the amount of hemoglobin, the concentration of blood can be calculated for each pixel through the calculation of the value of G/R.

The oxygen saturation of a blood vessel is the amount of oxyhemoglobin with respect to the total amount of hemoglobin (the total amount of oxyhemoglobin and reduced hemoglobin). The oxygen saturation can be calculated using the medical image of an object to be observed that is picked up with light having a specific wavelength range where a difference between a light absorption coefficient in oxyhemoglobin and a light absorption coefficient in reduced hemoglobin is large (for example, blue light having a wavelength of about 470±10 nm). Since the pixel values of B pixels representing a blood vessel have a correlation to oxygen saturation in a case where blue light having a wavelength of about 470±10 nm is used, the oxygen saturation of each of the pixels representing the blood vessel can be calculated using a table in which the pixel values of B pixels are associated with oxygen saturation, or the like.

A ratio of arteries is a ratio of the number of pixels of arteries to the number of pixels of all blood vessels. Likewise, a ratio of veins is a ratio of the number of pixels of veins to the number of pixels of all blood vessels. Arteries and veins can be distinguished using oxygen saturation. For example, in a case where blood vessels of which the oxygen saturation is 70% or more are referred to as arteries and blood vessels of which the oxygen saturation is lower than 70% are referred to as veins, extracted blood vessels can be classified into arteries and veins. Accordingly, a ratio of arteries and a ratio of veins can be calculated.

The concentration of an administered coloring agent is the concentration of a coloring agent sprayed on an object to be observed or a coloring agent injected into a blood vessel by intravenous injection. The concentration of an administered coloring agent is calculated as, for example, a ratio of the pixel value of a pixel corresponding to the color of the coloring agent to the pixel value of a pixel corresponding to a color other than the color of the coloring agent. For example, in a case where a coloring agent for blue coloration is administered, a ratio B/G of a B image to a G image, a ratio B/R of a B image to an R image, or the like represents the concentration of the coloring agent fixed (or temporarily adhering) to an object to be observed.

The travel pattern of blood vessels is vascular information about the travel direction of blood vessels. The travel pattern of blood vessels is, for example, the average angle (travel direction) of blood vessels with respect to a randomly set reference line, a variance of angles between the blood vessels and a randomly set reference line (a variation in the travel direction), or the like.

A blood flow rate (also referred to as blood flow velocity) in a blood vessel is the number of red blood cells passing per unit time. In a case where an ultrasonic probe is used together through the forceps channel of the endoscope 12 and the like, a blood flow rate in a blood vessel where the Doppler shift frequency of each of the pixels representing a blood vessel of the medical image is calculated using signals obtained by the ultrasonic probe can be obtained.

In the first to fifth embodiments, the invention has been applied to the medical image processing device that includes the image acquisition unit 54 and the image processing unit 61 provided in the processor device 16 and the user interface 19 and processes an endoscopic image as one of medical images. However, the invention can also be applied to a medical image processing device that processes medical images other than an endoscopic image. Further, the invention can also be applied to a diagnosis support device that supports diagnosis for a user by using a medical image. Furthermore, the invention can also be applied to a medical service support device that supports a medical service, such as a diagnosis report, by using a medical image.

It is preferable that the medical image is a normal light image obtained from the application of light in a white-light wavelength range or light in a plurality of wavelength ranges as the light in the white-light wavelength range.

It is preferable that the medical image is a special light image obtained from the application of light in a specific wavelength range and the light in the specific wavelength range is in a wavelength range narrower than the white-light wavelength range. It is preferable that the specific wavelength range is included in a blue-light wavelength range or a green-light wavelength range of a visible-light wavelength range. It is preferable that the specific wavelength range includes a wavelength range of 390 nm to 450 nm or 530 nm to 550 nm, and the light in the specific wavelength range has a peak wavelength in the wavelength range of 390 nm to 450 nm or 530 nm to 550 nm.

It is preferable that the specific wavelength range is included in a red-light wavelength range of the visible-light wavelength range. It is preferable that the specific wavelength range includes a wavelength range of 585 nm to 615 nm or 610 nm to 730 nm, and the light in the specific wavelength range has a peak wavelength in the wavelength range of 585 nm to 615 nm or 610 nm to 730 nm.

It is preferable that the specific wavelength range includes a wavelength range where an absorption coefficient in oxyhemoglobin and an absorption coefficient in reduced hemoglobin are different from each other and the light in the specific wavelength range has a peak wavelength in a wavelength range where an absorption coefficient in oxyhemoglobin and an absorption coefficient in reduced hemoglobin are different from each other. It is preferable that the specific wavelength range includes a wavelength range of 400±10 nm, 440±10 nm, 470±10 nm, or 600 nm to 750 nm and the light in the specific wavelength range has a peak wavelength in the wavelength range of 400±10 nm, 440±10 nm, 470±10 nm, or 600 nm to 750 nm.

It is preferable that the medical image is an in-vivo image of the inside of a living body and the in-vivo image includes information about the fluorescence of a fluorescent material present in the living body. It is preferable that the fluorescence is obtained from the irradiation of the inside of the living body with excitation light having a peak wavelength in the wavelength range of 390 to 470 nm.

It is preferable that the medical image is an in-vivo image of the inside of a living body and the specific wavelength range is an infrared wavelength range. It is preferable that the specific wavelength range includes a wavelength range of 790 nm to 820 nm or 905 nm to 970 nm, and the light in the specific wavelength range has a peak wavelength in the wavelength range of 790 nm to 820 nm or 905 nm to 970 nm.

It is preferable that the image acquisition unit includes a special-light-image acquisition section acquiring a special light image, which includes a signal in the specific wavelength range, on the basis of the normal light image obtained from the application of light in a white-light wavelength range or light in a plurality of wavelength ranges as the light in the white-light wavelength range and the medical image is the special light image.

It is preferable that the signal in the specific wavelength range is obtained from an arithmetic operation based on color information about RGB or CMY included in the normal light image.

It is preferable that the medical image processing device includes an arithmetic image generation section generating an arithmetic image from an arithmetic operation based on at least one of a normal light image, which is obtained from application of light in a white-light wavelength range or light in a plurality of wavelength ranges as the light in the white-light wavelength range, and a special light image, which is obtained from application of light in a specific wavelength range, and the medical image is the arithmetic image.

In the embodiment, the hardware structure of a processing unit, which performs various kinds of processing, such as the unnecessary region removal section 68, the region-of-interest extraction section 70, the diagnosis support information-calculation section 72, the region-of-interest change section 74, the region correction information-storage section 76, the feature quantity-selection section 94, or the diagnosis support information-storage section 95 included in the image processing unit 61, is various processors to be described later. Various processors include: a central processing unit (CPU) that is a general-purpose processor functioning as various processing units by executing software (program); a programmable logic device (PLD), which is a processor of which the circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

[Additional Claim 1]

A medical image processing device comprising:

an image acquisition unit that acquires a medical image as a medical image obtained from the image pickup of an object to be observed; and a region-of-interest extraction section that extracts regions of interest from the medical image and extracts a plurality of regions of interest from the medical image according to a plurality of region-of-interest extraction conditions different from each other.

[Additional Claim 2]

The medical image processing device according to Additional claim 1, wherein the region-of-interest extraction section calculates a first feature quantity from a first medical image and extracts the regions of interest on the basis of the first feature quantity, and a first region extraction ranges of the plurality of region-of-interest extraction conditions are different from each other.

[Additional Claim 3]

The medical image processing device according to Additional claim 1, wherein the region-of-interest extraction section calculates a first feature quantity and a second feature quantity from a first medical image and extracts the regions of interest on the basis of the first feature quantity and the second feature quantity, and a first region extraction ranges and a second region extraction ranges of the plurality of region-of-interest extraction conditions are different from each other.

[Additional Claim 4]

The medical image processing device according to any one of Additional claims 1 to 3, further comprising:

a diagnosis support information-calculation section that calculates diagnosis support information from each of the plurality of regions of interest.

[Additional Claim 5]

The medical image processing device according to any one of Additional claims 1 to 4, further comprising:

a diagnosis support information-storage section that stores the regions of interest and the diagnosis support information calculated from the regions of interest so that the regions of interest and the diagnosis support information are associated with each other.

EXPLANATION OF REFERENCES

10: endoscope system
12: endoscope
12*a*: insertion part
12*b*: operation part
12*c*: bendable part
12*d*: distal end part
12*e*: angle knob
12*f*: forceps inlet
13: zoom operation part
14: light source device
16: processor device
18: monitor
19: user interface
20: light source unit
22: light source control unit
30*a*: illumination optical system
30*b*: image pickup optical system
41: light guide
45: illumination lens
46: objective lens
47: zoom lens
48: image sensor
52: central control unit
54: image acquisition unit
56: DSP (Digital Signal Processor)
58: noise-reduction section
59: conversion section
61: image processing unit
66: display control unit
68: unnecessary region removal section
70: region-of-interest extraction section
72: diagnosis support information-calculation section
74: region-of-interest change section
76: region correction information-storage section
80: diagnosis support information
82: pointer
86: slide bar
88: slider
90: slide bar
92: slider
94: feature quantity-selection section
95: diagnosis support information-storage section
96: slide bar
98: slider

What is claimed is:

1. A medical image processing device comprising:
   an image acquisition unit that acquires a medical image obtained from image pickup of an object to be observed;
   a region-of-interest extraction section that extracts a first region of interest as a region of interest from the medical image;
   a region-of-interest change section that performs correction processing for correcting the first region of interest to a second region of interest; and
   a user interface that receives an instruction given to the region-of-interest change section by a user,
   wherein a first medical image and a second medical image different from each other are included in the medical image,
   the region-of-interest change section performs the correction processing on a region of interest extracted from the first medical image,
   the region-of-interest extraction section extracts a region of interest from the second medical image by using region correction information about the correction processing,
   the region-of-interest change section performs the correction processing by changing a region-of-interest extraction condition for extraction of the region of interest,
   the region-of-interest extraction section calculates a first feature quantity from the medical image and extracts a region where the first feature quantity is in a first region extraction range as the region of interest, and
   the region-of-interest extraction condition is a condition about the first region extraction range.

2. A medical image processing device comprising:
   an image acquisition unit that acquires a medical image obtained from image pickup of an object to be observed;
   a region-of-interest extraction section that extracts a first region of interest as a region of interest from the medical image;
   a region-of-interest change section that performs correction processing for correcting the first region of interest to a second region of interest; and
   a user interface that receives an instruction given to the region-of-interest change section by a user,
   wherein the medical image is a normal light image that is obtained from application of light in a white-light wavelength range or light in a plurality of wavelength ranges as the light in the white-light wavelength range,
   the region-of-interest change section performs the correction processing by changing a region-of-interest extraction condition for extraction of the region of interest,
   the region-of-interest extraction section calculates a first feature quantity from the medical image and extracts a region where the first feature quantity is in a first region extraction range as the region of interest, and
   the region-of-interest extraction condition is a condition about the first region extraction range.

3. A medical image processing device comprising:
   an image acquisition unit that acquires a medical image obtained from image pickup of an object to be observed;
   a region-of-interest extraction section that extracts a first region of interest as a region of interest from the medical image;
   a region-of-interest change section that performs correction processing for correcting the first region of interest to a second region of interest; and
   a user interface that receives an instruction given to the region-of-interest change section by a user,
   wherein the medical image is a special light image that is obtained from application of light in a specific wavelength range,
   the light in the specific wavelength range is in a wavelength range narrower than a white-light wavelength range,
   the region-of-interest change section performs the correction processing by changing a region-of-interest extraction condition for extraction of the region of interest,
   the region-of-interest extraction section calculates a first feature quantity from the medical image and extracts a region where the first feature quantity is in a first region extraction range as the region of interest, and
   the region-of-interest extraction condition is a condition about the first region extraction range.

4. The medical image processing device according to claim 1,
   wherein the correction processing includes at least one of enlargement, reduction, or position change of the first region of interest.

5. The medical image processing device according to claim 1,
   wherein the region-of-interest change section performs addition processing for adding a third region of interest to a position different from a position of the first region of interest or deletion processing for deleting the first region of interest.

6. The medical image processing device according to claim 5,
   wherein the user interface receives an instruction to perform the correction processing, the addition processing, or the deletion processing.

7. The medical image processing device according to claim 1,
   wherein the region-of-interest extraction section calculates a first feature quantity and a second feature quantity from the medical image and extracts the region of interest on the basis of a region where the first feature quantity is in a first region extraction range and a region where the second feature quantity is in a second region extraction range, and
   the region-of-interest extraction condition is conditions about the first region extraction range and the second region extraction range.

8. The medical image processing device according to claim 1,
   wherein the user interface receives an instruction to change the region-of-interest extraction condition.

9. The medical image processing device according to claim 1, further comprising:
   a feature quantity-selection section that performs feature quantity-selection processing for selecting a feature quantity, which is to be used for the extraction of the region of interest, from a plurality of feature quantities, and
   wherein the region-of-interest extraction section calculates the feature quantity selected from the medical image by the feature quantity-selection section and extracts the region of interest on the basis of the calculated feature quantity.

10. The medical image processing device according to claim 9,
    wherein the user interface receives an instruction for the feature quantity-selection processing.

11. The medical image processing device according to claim 1, further comprising:
a region correction information-storage section that stores the region correction information.

12. The medical image processing device according to claim 1, further comprising:
a diagnosis support information-calculation section that calculates diagnosis support information from the first region of interest or the second region of interest.

13. The medical image processing device according to claim 1,
wherein the medical image is a normal light image that is obtained from application of light in a white-light wavelength range or light in a plurality of wavelength ranges as the light in the white-light wavelength range.

14. The medical image processing device according to claim 1,
wherein the medical image is a special light image that is obtained from application of light in a specific wavelength range, and
the light in the specific wavelength range is in a wavelength range narrower than a white-light wavelength range.

15. The medical image processing device according to claim 14,
wherein the specific wavelength range is included in a blue-light wavelength range or a green-light wavelength range of a visible-light wavelength range.

16. The medical image processing device according to claim 15,
wherein the specific wavelength range includes a wavelength range of 390 nm to 450 nm or 530 nm to 550 nm, and the light in the specific wavelength range has a peak wavelength in a wavelength range of 390 nm to 450 nm or 530 nm to 550 nm.

17. The medical image processing device according to claim 14,
wherein the specific wavelength range is included in a red-light wavelength range of a visible-light wavelength range.

18. The medical image processing device according to claim 17,
wherein the specific wavelength range includes a wavelength range of 585 nm to 615 nm or 610 nm to 730 nm, and the light in the specific wavelength range has a peak wavelength in a wavelength range of 585 nm to 615 nm or 610 nm to 730 nm.

19. The medical image processing device according to claim 14,
wherein the specific wavelength range includes a wavelength range where an absorption coefficient in oxyhemoglobin and an absorption coefficient in reduced hemoglobin are different from each other and the light in the specific wavelength range has a peak wavelength in a wavelength range where an absorption coefficient in oxyhemoglobin and an absorption coefficient in reduced hemoglobin are different from each other.

20. The medical image processing device according to claim 19,
wherein the specific wavelength range includes a wavelength range of 400±10 nm, 440±10 nm, 470±10 nm, or 600 nm to 750 nm and the light in the specific wavelength range has a peak wavelength in a wavelength range of 400±10 nm, 440±10 nm, 470±10 nm, or 600 nm to 750 nm.

21. The medical image processing device according to claim 14,
wherein the medical image is an in-vivo image of an inside of a living body, and
the in-vivo image includes information about fluorescence of a fluorescent material present in the living body.

22. The medical image processing device according to claim 21,
wherein the fluorescence is obtained from irradiation of the inside of the living body with excitation light having a peak wavelength in a wavelength range of 390 to 470 nm.

23. The medical image processing device according to claim 14,
wherein the medical image is an in-vivo image of an inside of a living body, and
the specific wavelength range is an infrared wavelength range.

24. The medical image processing device according to claim 23,
wherein the specific wavelength range includes a wavelength range of 790 nm to 820 nm or 905 nm to 970 nm, and the light in the specific wavelength range has a peak wavelength in a wavelength range of 790 nm to 820 nm or 905 nm to 970 nm.

25. The medical image processing device according to claim 1,
wherein the image acquisition unit includes a special-light-image acquisition section acquiring a special light image, which includes a signal in a specific wavelength range, on the basis of a normal light image obtained from application of light in a white-light wavelength range or light in a plurality of wavelength ranges as the light in the white-light wavelength range, and
the medical image is the special light image.

26. The medical image processing device according to claim 25,
wherein the signal in the specific wavelength range is obtained from an arithmetic operation based on color information about RGB or CMY included in the normal light image.

27. The medical image processing device according to claim 1, further comprising:
an arithmetic image generation section that generates an arithmetic image from an arithmetic operation based on at least one of a normal light image, which is obtained from application of light in a white-light wavelength range or light in a plurality of wavelength ranges as the light in the white-light wavelength range, or a special light image, which is obtained from application of light in a specific wavelength range,
wherein the medical image is the arithmetic image.

28. An endoscope system comprising:
the medical image processing device according to claim 1; and
an endoscope that applies at least one of light in a white-light wavelength range or light in a specific wavelength range.

29. A diagnosis support device comprising:
the medical image processing device according to claim 1.

30. A medical service support device comprising:
the medical image processing device according to claim 1.

* * * * *